US012738347B2

United States Patent
(12) United States Patent
Ryuzaki et al.

(10) Patent No.: US 12,738,347 B2
(45) Date of Patent: Sep. 15, 2026

(54) METHOD FOR GENERATING SPECTRAL DATA PERTAINING TO MICROPARTICLE SAMPLE, METHOD FOR ANALYZING MICROPARTICLES, METHOD FOR DISTINGUISHING MICROPARTICLES, METHOD FOR ASSESSING WHETHER CANCER-CELL-DERIVED EXOSOMES ARE PRESENT, SUBSTRATE FOR MEASURING SPECTRUM OF MICROPARTICLES, DEVICE FOR MEASURING SPECTRUM OF MICROPARTICLES, AND APPARATUS FOR MEASURING SPECTRUM OF MICROPARTICLES

(71) Applicants: National University Corporation Hokkaido University, Hokkaido (JP); Osaka University, Osaka (JP)

(72) Inventors: Sou Ryuzaki, Sapporo (JP); Rintaro Matsuda, Kanagawa (JP); Masateru Taniguchi, Osaka (JP); Yuki Komoto, Osaka (JP)

(73) Assignees: National University Corporation Hokkaido University, Hokkaido (JP); Osaka University, Osaka (JP)

( * ) Notice: Subject to any disclaimer, the term of this patent is extended or adjusted under 35 U.S.C. 154(b) by 167 days.

(21) Appl. No.: 18/711,248

(22) PCT Filed: Nov. 18, 2022

(86) PCT No.: PCT/JP2022/042861
§ 371 (c)(1),
(2) Date: May 17, 2024

(87) PCT Pub. No.: WO2023/090421
PCT Pub. Date: May 25, 2023

(65) Prior Publication Data

US 2025/0014684 A1 Jan. 9, 2025

(30) Foreign Application Priority Data

Nov. 19, 2021 (JP) ................................ 2021-188402

(51) Int. Cl.
*G16C 20/20* (2019.01)
*G16C 20/70* (2019.01)

(52) U.S. Cl.
CPC ............ *G16C 20/20* (2019.02); *G16C 20/70* (2019.02)

(58) Field of Classification Search
CPC .. C12Q 1/02; G01N 15/1429; G01N 15/1434; G01N 2015/1006;
(Continued)

(56) References Cited

U.S. PATENT DOCUMENTS 6,677,160 B1 * 1/2004 Stockman .............. C40B 40/04 435/7.1
2009/0311717 A1 12/2009 De Sonneville et al.
(Continued)

FOREIGN PATENT DOCUMENTS

EP 2517008 B1 11/2016
JP 2020-106370 A 7/2020
(Continued)

OTHER PUBLICATIONS

Extended European search report of application No. 22895702.3 dated May 30, 2025.
(Continued)

*Primary Examiner* — Hina F Ayub
(74) *Attorney, Agent, or Firm* — Calfee, Halter & Griswold LLP

(57) ABSTRACT

A method for generating spectral data according to the present invention involves generating spectral data pertaining to a microparticle sample that includes at least one
(Continued)

microparticle, wherein: the method includes a step for acquiring a measurement spectrum from microparticles disposed within a through-hole in a substrate; the through-hole has an inclined structure in which the width continuously decreases from one surface of the substrate toward the other surface thereof; at least part of the inner surface of the through-hole is configured from a metal that exhibits plasmon resonance; and in the step for acquiring the measurement spectrum, the measurement spectrum is acquired while the interior of the through-hole is irradiated with light.

16 Claims, 14 Drawing Sheets

(58) Field of Classification Search
CPC ......... G01N 33/4833; G01N 33/48707; G01N 33/48721; G16C 20/20; G16C 20/70
See application file for complete search history.

(56) References Cited

U.S. PATENT DOCUMENTS

| | | | | |
|---|---|---|---|---|
| 2011/0036994 | A1 | 2/2011 | Frayling | |
| 2020/0110084 | A1 | 4/2020 | Takeuchi et al. | |
| 2021/0140891 | A1 | 5/2021 | Okuno et al. | |
| 2021/0372933 | A1* | 12/2021 | Xie | A61B 5/0075 |
| 2024/0219236 | A1* | 7/2024 | Nozawa | G01J 3/44 |

FOREIGN PATENT DOCUMENTS

| | | | |
|---|---|---|---|
| WO | 2009/030953 | A1 | 3/2009 |
| WO | 2018/221271 | A1 | 12/2018 |
| WO | 2019/117177 | A1 | 6/2019 |

OTHER PUBLICATIONS

Haiying Zhang, et al., "Identification of distinct nanoparticles and subsets of extracellular vesicles by asymmetric flow field-flow fractionation", Nature Cell Biology, vol. 20, pp. 332-343,Mar. 2018.
Ayuko Hoshino, et al., "Tumour exosome integrins determine organotropic metastasis", Nature, vol. 527, pp. 329-335, Nov. 19, 2015.
Ayuko Hoshino, et al., "Extracellular Vesicle and Particle Biomarkers Define Multiple Human Cancers", Cell, vol. 182, pp. 1044-1061, Aug. 20, 2020.
Shilian Dong et al., "Beehive-Inspired Macroporous SERS Probe for Cancer Detection through Capturing and Analyzing Exosomes in Plasma", ACS Appl. Mater. Interfaces, vol. 12, pp. 5136-5146 (2020).
Mustafa H. Chowdhury, et al., "Use of surface-enhanced Raman spectroscopy for the detection of human integrins", Journal of Biomedical Optics, vol. 11, 024004, Mar./Apr. 2006.
Kazunori Matsui, et al., "Raman Spectra of Silica Gel Prepared from Triethoxysilane and Tetraethoxysilane by the Sol- Gel Method", Journal of the Ceramic Society of Japan, vol. 106, pp. 528-530 (1998).
Rintaro Matsuda et al., Plasmonic properties of inverted cone shaped plasomonic nanopores (Feb. 28, 2020).
Carmicael, J. et al., Label-free characterization of exosome via surface enhanced Raman spectroscopy for the early detection of pancreatic cancer, Nanomedicine: Nanotechnology, Biology, and Medicine, 2018, 16, 88-96 P92-93.
Huang. J. et al., Distinguishing Cancerous Liver Cells Using Surface-Enhanced Raman Spectroscopy, Technology in Cancer Research & Treatment, Nov. 28, 2014, 15(1), 36/43 Fig.4.
International Search Report from PCT/JP2022/042861 dated Dec. 27, 2022.

* cited by examiner

METHOD FOR GENERATING SPECTRAL DATA PERTAINING TO MICROPARTICLE SAMPLE, METHOD FOR ANALYZING MICROPARTICLES, METHOD FOR DISTINGUISHING MICROPARTICLES, METHOD FOR ASSESSING WHETHER CANCER-CELL-DERIVED EXOSOMES ARE PRESENT, SUBSTRATE FOR MEASURING SPECTRUM OF MICROPARTICLES, DEVICE FOR MEASURING SPECTRUM OF MICROPARTICLES, AND APPARATUS FOR MEASURING SPECTRUM OF MICROPARTICLES

CROSS-REFERENCE TO RELATED APPLICATION

The present application is the U.S. National Stage of International Application No. PCT/JP2022/042861, filed on Nov. 18, 2022, which claims priority to Japanese Application No. 2021-188402, filed Nov. 19, 2021, the contents of which are incorporated herein by reference in their entireties for all purposes.

TECHNICAL FIELD

The present invention relates to a generation method (production method) for spectral data of a microparticle sample. The present invention also relates to an analysis method for a microparticle; a discrimination method of discriminating a yet-to-be discriminated microparticle; a determination method of determining presence or absence of a cancer cell-derived exosome in a body fluid-derived sample containing an exosome; a substrate for measuring a spectrum of a microparticle; a device for measuring a spectrum of a microparticle; and an apparatus for measuring a spectrum of a microparticle.

BACKGROUND ART

In various fields, an analysis of microparticles or an analysis using microparticles is made based on components contained in the microparticles. For example, biogenic microparticles with a length less than or equal to 5 μm, such as particulate small bacteria and the like, exosomes, and viruses, are subjected to determination of type or determination as to the possibility of a disease of a body, from which biogenic microparticles are derived, by clarifying characteristic molecules present on a membrane surface. An analysis of air pollution situation is performed by using a component analysis of PM2.5 that is microparticles, dispersed in the atmosphere, with a diameter less than or equal to 2.5 μm.

Among methods for identifying components contained in microparticles, spectral measurement is a technique capable of making a nondestructive analysis. Particularly, a Raman spectrum is to observe a signal based on the vibrations of molecules that make up a substance and allows to obtain information based on components that make up microparticles. Raman scattered light is extremely weak; however, in recent years, a further high-sensitivity analysis is possible by surface enhanced Raman scattering (SERS) or the like. SERS is a method using a phenomenon in which the intensity of Raman scattered light of a molecule increases due to localized surface plasmon resonance (SPR) on a metal, such as silver and gold, having a rough surface. PTL 1 describes an apparatus that analyzes molecules of polynucleotide or the like by using SPR.

On the other hand, a method of discriminating the type of a target greater than microparticles with a length less than or equal to 5 μm is known. For example, PTL 2 describes a method of discriminating the type of cells contained in a sample by using a Raman spectrum. With the method described in PTL 2, a Raman spectrum is acquired from a yet-to-be discriminated cell, a plurality of degrees of coincidence respectively indicating the degrees to which the Raman spectrum of the yet-to-be discriminated cell coincides with spectra of a plurality of principal components obtained through a principal component analysis of a plurality of Raman spectra including Raman spectra respectively obtained one by one from a plurality of cells of which the types are identified, and the type of the yet-to-be discriminated cell is discriminated based on classification of the degrees of coincidence.

CITATION LIST

Patent Literature

PTL 1
WO 2009/030953
PTL 2
WO 2019/117177

SUMMARY OF INVENTION

Technical Problem

In the analysis method described in PTL 2, an analysis is performed by acquiring a Raman spectrum from a yet-to-be discriminated microparticle. Actually, in the paragraph [0037] and FIG. 4 of PTL 2, eukaryotic animal cells, such as rat basophilic leukemia cells (RBL) and Chinese hamster ovary cells (CHO), are used, and the particle diameters of those cells range from about 10 μm to about 30 μm. In the paragraph of PTL 2, a Raman scattered light measurement apparatus that acquires a Raman spectrum one by one from each cell with such a large particle diameter while changing the cell to which laser light is applied is described. However, the apparatus described in PTL 2 is an apparatus that cannot be applied to microparticles with a length less than or equal to 5 μm and is difficult to be directly converted to a case where the size of microparticles is small.

Furthermore, in a sample containing a large amount of microparticles, an accurate result is possibly not obtained from an analysis based on data from only one of those microparticles. There can be a case where it is not possible to make an intended analysis based on a measurement result of one or limited number of microparticles in an available sample. For example, even when there is a component peculiar to exosomes derived from cancer cells, the cancer cell-derived exosomes are some of exosomes contained in a body fluid used for inspection, so it is not possible to perform proper determination using the peculiar component from the measurement result of one or some exosomes. On the other hand, with a further general technique to collectively measure a certain amount of microparticles, information of components contained in only some microparticles in a sample is less likely to be reflected.

PTL 2 describes discrimination using principal component analysis results of a plurality of spectra respectively obtained from a plurality of cells of which the types are identified. However, to make it possible to make a further reliable analysis, a method of easily obtaining a larger amount of a plurality of spectra is desired.

An object of the present invention is to provide a generation method for spectral data for an analysis of microparticles with a length less than or equal to 5 μm or an analysis using microparticles with a length less than or equal to 5 μm. Another object of the present invention is to provide a substrate, a device, and an apparatus for measuring a spectrum of a microparticle, which can be used in the above method. Further another object of the present invention is to, using the above method, provide an analysis method for a microparticle, a discrimination method of discriminating a yet-to-be discriminated microparticle, and a determination method of determining presence or absence of a cancer cell-derived exosome in a body fluid-derived sample containing an exosome.

Solution to Problem

The inventors diligently studied to solve the above problem, completed a substrate capable of measuring a microparticle with a length less than or equal to 5 μm with high sensitivity with a technique totally different from the measurement method of PTL 2 and found a method of efficiently generating and acquiring a measured spectrum of each microparticle for a large amount of microparticles by using the substrate. Then, a further study had been performed over and over based on this method, and completion of the present invention was reached.

Specifically, the present invention is as follows.

[1] A generation method for spectral data of a microparticle sample containing at least one microparticle, the generation method including: acquiring a measured spectrum from a microparticle placed in a through-hole of a substrate, in which the through-hole has a tapered structure in which a width continuously reduces from one surface of the substrate to another surface of the substrate, at least part of an inner surface of the through-hole is made of a metal that exhibits plasmon resonance, and the acquiring a measured spectrum includes acquiring the measured spectrum while applying light into the through-hole.

[2] The generation method according to [1], in which the acquiring a measured spectrum includes acquiring a measured spectrum from each of a plurality of microparticles in the microparticle sample, and the spectral data is a bundle of a plurality of measured spectra.

[3] The generation method according to [1], in which a length of the microparticle ranges from 10 nm to 5 μm.

[4] The generation method according to [2], in which the acquiring a measured spectrum includes causing the plurality of microparticles to pass through the through-hole one by one, and acquiring the measured spectrum from each of the plurality of microparticles.

[5] The generation method according to [1], in which the acquiring a measured spectrum includes moving the microparticle, dispersed in a liquid, into the through-hole with one or more methods selected from the group consisting of electrophoresis, dielectrophoresis, optical tweezers, Brownian movement, and Coulomb interaction.

[6] The generation method according to any one of [1] to [5], in which the measured spectrum is a Raman spectrum.

[7] The generation method according to any one of [1] to [5], in which the measured spectrum is a fluorescent spectrum.

[8] An analysis method for a microparticle, including making a statistical analysis of the spectral data acquired with the generation method according to [2].

[9] The analysis method according to [8], in which the making a statistical analysis of the spectral data includes forming a collection of peaks having a high correlation coefficient with each other between the plurality of measured spectra of the spectral data, and identifying at least one component contained in the microparticles by comparing the obtained collection of peaks with a spectrum of a known object.

[10] The analysis method according to [8], in which the making a statistical analysis of the spectral data includes making a multivariate analysis on the plurality of measured spectra of the spectral data, and identifying at least one component contained in the microparticles by comparing a spectrum, obtained through the multivariate analysis, with a spectrum of a known object.

[11] A discrimination method of discriminating a yet-to-be discriminated microparticle, the discrimination method including: acquiring a measured spectrum of each of a plurality of microparticles A of which a type has been turned out and a measured spectrum of each of a plurality of microparticles B of which another type has been turned out, with the generation method according to [2]; making a principal component analysis of spectral data including the measured spectra of the plurality of microparticles A and the measured spectra of the plurality of microparticles B and obtaining an index to discriminate the measured spectrum of the microparticle A and the measured spectrum of the microparticle B from scores of two or more principal components; acquiring a measured spectrum from each of one or more yet-to-be discriminated microparticles in a microparticle sample with the generation method according to [1] or [2]; calculating scores of the two or more principal components for the measured spectrum of the yet-to-be discriminated microparticle; and performing discrimination by comparing the scores of the yet-to-be discriminated microparticle with the index, in which a length of the yet-to-be discriminated microparticle ranges from 10 nm to 5 μm.

[12] The discrimination method according to [11], in which the yet-to-be discriminated microparticle is an exosome, the microparticles A are cancer cell-derived exosomes, the microparticles B are normal cell-derived exosomes, and the performing discrimination includes discriminating whether the exosome serving as the yet-to-be discriminated microparticle is derived from a cancer cell.

[13] A determination method of determining presence or absence of a cancer cell-derived exosome in a body fluid-derived sample containing exosomes, the determination method including: generating spectral data made up of a plurality of measured spectra respectively obtained from a plurality of exosomes in the sample with the generation method according to [2]; obtaining a correlation coefficient between a signal having a local maximum at 1087 $cm^{-1\pm5}$ $cm^{-1}$ and a signal having a local maximum at 1435 $cm^{-1\pm5}$ $cm^{-1}$ between the plurality of measured spectra; and determining that a cancer cell-derived exosome is present in the sample when the correlation coefficient is higher than or equal to a certain value.

[14] A substrate for measuring a spectrum of a microparticle, the substrate including: a through-hole extending through from one surface of the substrate to the other surface of the substrate, in which the through-hole has a size by which the microparticle is allowed to pass one by one, at least part of an inner surface of the through-hole is made of a metal that exhibits plasmon resonance, and the through-hole has a tapered structure in which a width continuously reduces from the one surface of the substrate to the other surface of the substrate.

[15] The substrate according to [14], in which the through-hole has a frustum shape.

[16] The substrate according to [15], in which an equivalent circle diameter of an opening portion of the through-hole in the other surface of the substrate ranges from 10 nm to 5 μm.

[17] A device for measuring a spectrum of a microparticle, the device including: the substrate according to any one of to [16]; a first liquid tank including an inner wall including at least a portion having the through-hole at the one surface of the substrate; and a second liquid tank including an inner wall including at least a portion having the through-hole in the other surface of the substrate.

[18] An apparatus for measuring a spectrum of a microparticle, the apparatus including: the device according to [17]; a guiding section for causing the microparticle to pass through the through-hole one by one; a light source; and a detecting section that acquires a measured spectrum by measuring light that is generated when light from the light source is applied to the microparticle in the through-hole.

[19] The apparatus according to [18], in which the measured spectrum is a Raman spectrum.

[20] The apparatus according to [18], in which the measured spectrum is a fluorescent spectrum.

Advantageous Effects of Invention

According to the present invention, a new generation method for spectral data for an analysis of microparticles with a length less than or equal to 5 μm or an analysis using microparticles with a length less than or equal to 5 μm is provided. According to the present invention, a substrate, a device, and an apparatus for measuring a spectrum of a microparticle, which can be used in the above method, are provided. According to the present invention, using the above method, an analysis method for a microparticle, a discrimination method of discriminating a yet-to-be discriminated microparticle, and a determination method of determining presence or absence of a cancer cell-derived exosome in a body fluid-derived sample containing an exosome are provided.

DESCRIPTION OF EMBODIMENTS

Figure 1A:
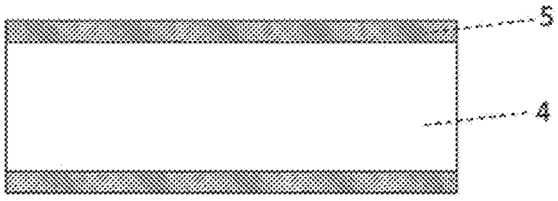
FIGS. 1A to 1C are views showing a manufacturing procedure of a substrate used in an embodiment.

Hereinafter, the present invention will be described in detail. The description of structural requirements described below can be made based on typical embodiments or specific examples, and the present invention is not limited to those embodiments. In the specification, a numeric value range expressed by using "to" means a range including numeric values written before and after "to" as a lower limit and an upper limit.

<Generation Method for Spectral Data of Microparticle Sample>

A generation method for spectral data of a microparticle sample according to the present invention (hereinafter, referred to as a generation method according to the present invention) is a generation method (production method) for spectral data of a microparticle sample containing at least one microparticle, and includes obtaining a measured spectrum from a microparticle placed in a through-hole of a substrate. As will be described later, the through-hole has a tapered structure in which a width continuously reduces from one surface of the substrate to the other surface of the substrate, and at least part of an inner surface of the through-hole is made of a metal that exhibits plasmon resonance. The acquiring a measured spectrum includes acquiring a measured spectrum while applying light into the through-hole. When the microparticle sample contains a plurality of microparticles, the acquiring a measured spectrum may include acquiring a measured spectrum from each of the plurality of microparticles in the microparticle sample. In this case, spectral data is a bundle of a plurality of measured spectra.

The present invention relates to a generation method for spectral data of a microparticle sample. More specifically, the present invention relates to a generation method for spectral data of a microparticle sample for making an analysis of a microparticle or an analysis using a microparticle, based on a component contained in the microparticle. In the specification, a "component contained in a microparticle" is not limited and may be a specific one component or substantially all the components. A "component contained in a microparticle" is selected as needed in accordance with a type of spectrum acquired and a purpose of an analysis. A component contained in a microparticle to be analyzed may be a component contained in any part of the microparticle. Depending on a type of spectrum acquired, for spectral data that can be acquired without destruction of a microparticle, it is possible to make an analysis of a component contained at the surface of the microparticle.

When the microparticle sample contains a plurality of microparticles, the generation method according to the present invention can provide the spectral data of the microparticle sample as a bundle of measured spectra based on the respective microparticles. Ordinarily, spectral data of a microparticle sample is that a certain amount of microparticles are collectively measured, so data is averaged, and information of a component contained in only some of microparticles in the sample is less likely to be reflected. Conventionally, an analysis based on a measured spectrum of a microparticle has been difficult. On the other hand, even in an analysis based on a measured spectrum of a cell of which the length exceeds 10 μm, the analysis is limited to the one using a measured spectrum of each of limited-number cells, that is, about one or several cells, as described in PTL 2.

With the generation method according to the present invention, by providing spectral data of a microparticle sample containing a plurality of microparticles as a bundle of measured spectra based on the respective microparticles, an analysis with a statistical process is possible. It is also possible to detect a component that cannot be conventionally detected, as a component contained in various microparticles. Furthermore, determination impossible with an existing method, such as determination based on the amount of microparticles containing a specific component among microparticles in a sample, is possible. Hereinafter, spectral data generated by the generation method according to the present invention (a bundle of measured spectra based on respective microparticles) is also referred to as a "new database obtained by the present invention".

(Microparticle)

In the specification, the term "microparticle" means a particle with a length of 10 nm to 5 μm. The shape of the microparticle is not limited and may be, for example, a spherical shape, an elliptical shape, a cylindrical shape, a cubic shape, a pyramidal shape, another polyhedral shape, a conical shape, an indefinite shape, or the like.

In the specification, it is assumed that the length of a microparticle means the length of the longest line (long axis) of lines that connect two points that are intersections of a line passing through the center of a cross section of the microparticle with an outer circumference of the cross section. In the present invention, the length of the microparticle preferably ranges from 10 nm to 3 μm, more preferably ranges from 10 nm to 1 μm, particularly preferably ranges from 30 nm to 500 nm, and more particularly preferably ranges from 50 nm to 200 nm.

In the specification, the shortest line (short axis) of lines that connect two points that are intersections of a line passing through the center of a cross section of the microparticle with an outer circumference of the cross section preferably ranges from 1 nm to 5 μm, more preferably ranges from 3 nm to 3 μm, particularly preferably ranges from 5 nm to 1 μm, further more preferably ranges from 10 nm to 500 nm, further more particularly preferably ranges from 30 nm to 300 nm, most preferably ranges from 50 nm to 200 nm. When microparticles are caused to pass through the through-hole of the substrate having the through-hole one by one, it is preferable to set not only the range of the length (long axis) of each microparticle but also the range of the short axis to the above-described preferable ranges.

The ratio of the length (long axis) to the short axis (aspect ratio) of each microparticle, for example, may range from 99:1 to 50:50, preferably ranges from 90:10 to 50:50, more preferably ranges from 80:20 to 50:50, particularly preferably ranges from 70:30 to 50:50, and more particularly preferably ranges from 60:40 to 50:50. Microparticles with a relatively small aspect ratio rather than long-slender microparticles with a large aspect ratio, such as polynucleotide and other polymer molecules, are preferable from the viewpoint that it is easy to pass microparticles one by one through the through-hole of the substrate having the through-hole.

A microparticle may be made up of a single component or may be made up of a plurality of components. The generation method according to the present invention is highly significant when targeting at particularly a microparticle made up of a plurality of components. Examples of the microparticle include a biogenic microparticle derived from living things and an inorganic microparticle. Examples of the biogenic microparticle include a particulate small bacterium and the like, a cell organelle, such as a mitochondrion, a virus, and an exosome. Among biogenic microparticles, a biogenic microparticle preferably has a lipid bilayer membrane structure and a virus and an exosome are more preferable from the viewpoint that a microparticle is caused to pass one by one through a through-hole of the substrate and a measured spectrum is acquired at the location of the through-hole. Examples of the inorganic microparticle include PM2.5.

Examples of the component contained in the biogenic microparticle include lipid, protein, and sugar chain. Examples of the component contained in the inorganic microparticle include not only a carbon component, a nitrate, a sulfate, and an ammonium salt but also silicon, sodium, and aluminum.

Among these, a microparticle is preferably a virus, an exosome, or a particle with a diameter less than or equal to 2.5 μm, dispersed in the atmosphere, from the viewpoint of having common properties in terms that the length of each microparticle ranges from 10 nm to 3 μm and the aspect ratio falls within a preferable range.

Examples of a particulate small bacterium and the like include a fungus, a virus, and a mycoplasma. A particulate small bacterium and the like is typically a bacterium and the like with a particle diameter of 100 nm to 5 μm and preferably a bacterium and the like with a particle diameter of 100 nm to 3 μm. Examples of the component contained in a bacterium and the like that can be analyzed with spectral data obtained with the generation method according to the present invention include membrane protein. Discrimination of the type and state of bacterium and the like is possible by making an analysis of membrane protein.

Coronaviruses, noroviruses, influenza viruses, Ebola viruses, and the like are known as viruses. Viruses are typically illustrated as viruses with a particle diameter of 10 nm to 1 μm. Examples of the component contained in a virus that can be analyzed by using spectral data obtained with the generation method according to the present invention include spike protein at the surface. Through an analysis of spike protein, discrimination of the type of a virus is possible, and identification of variants and the like is also possible.

In the specification, an exosome is used synonymously with an "extracellular vesicle". An extracellular vesicle is defined as a "particle that is released from a cell, having no nucleus (cannot be duplicated), and surrounded by a lipid bilayer membrane". Examples of the component contained in an exosome that can be analyzed by using spectral data obtained with the generation method according to the present invention include a component in the lipid bilayer membrane or a component present at the surface of the lipid bilayer membrane.

In recent years, the "exosome" is one type of extracellular vesicle, and an extracellular vesicle is classified into an "exosome", a "microvesicle", and an "apoptotic body" by production structure and size. An exosome is an endosome-derived vesicle and has a particle diameter of about 50 nm to about 150 nm. A microvesicle is a vesicle directly secreted from a cell and has a particle diameter of about 0.1 μm to about 1 μm. An apoptotic body is a cellular fragment that occurs from a cell death and has a particle diameter of about 1 μm to about 4 μm. However, in the specification, the exosome may be an "exosome", a "microvesicle", or an "apoptotic body", or a mixture of them. An exosome may be, for example, a mixture of "exosome" and "microvesicle".

Exosomes are microparticles secreted from cells and present in a body fluid. Because exosomes include information of cells from which the exosomes are secreted, exosomes become a focus of attention as a biomarker for diseases including cancers. Particularly, it is possible to predict the type of cancer and a metastasis destination of the cancer by investigating components present at the surface of the lipid bilayer membrane of an exosome, specifically, molecules of protein, lipid, sugar chain, and the like (NPL 1 to 3). However, conventionally, when an exosome is measured with Raman spectroscopy, a spectrum that represents all the information of a plurality of components including protein, lipid, sugar chain, and the like, so it is difficult to make an analysis of a specific component. By using the generation method for spectral data according to the present invention, it is possible to make an analysis of a specific component of an exosome using Raman spectroscopy, so it is conceivable to make it possible to determine a marker of a disease, such as a cancer.

[NPL 1] Haiying Zhang, et al., "Identification of distinct nanoparticles and subsets of extracellular vesicles by asymmetric flow field-flow fractionation", Nature Cell Biology, Vol. 20, pp. 332-343.

[NPL 2] Ayuko Hoshino, et al., "Tumour exosome integrins determine organotropic metastasis", Nature, Vol. 527, pp. 329-335.

[NPL 3] Ayuko Hoshino, et al., "Extracellular Vesicle and Particle Biomarkers Define Multiple Human Cancers", Cell, Vol. 182, pp. 1044-1061.

Cancer-derived exosomes are contained in a body fluid, such as blood, urine, and saliva. Therefore, inspection and diagnosis using exosomes, different from the existing one, can be carried out by using a noninvasive sample. A body fluid contains biogenic components other than exosomes. Because those components are noise for measurement, exosomes may be separated from a sample in accordance with a known procedure as shown in, for example, an embodiment (described later). Examples of the type of cancer that secretes exosomes include stomach cancer, esophageal cancer, lung cancer, liver cancer, biliary cancer, pancreatic cancer, colon cancer, ovarian cancer, prostate cancer, bladder cancer, breast cancer, glioma, glioblastoma, melanoma, and medulloblastoma.

PM2.5 is a microparticle with a diameter (particle diameter, preferably a long axis) less than or equal to 2.5 μm and dispersed in the atmosphere. PM2.5 is made up of salts, such as sulfates and nitrates, silica components, metal components, black carbon, and various organic compounds and is suspended mainly as an aerosol. With spectral data obtained with the generation method according to the present invention, not only components at the surface of PM2.5 but also components that make up PM2.5 can be analyzed. There are various compositions of PM2.5 according to environments. It is possible to determine the origin of PM2.5, the influence of PM2.5 on bodies, and the like by investigating a composition of PM2.5.

(Microparticle Sample)

The generation method for spectral data of a microparticle sample according to the present invention includes obtaining a measured spectrum from each of n microparticles of a microparticle sample containing a plurality of microparticles. Examples of the microparticle sample include a culture medium for cells, a suspension for cells, a suspension containing a body fluid containing exosomes or containing exosomes separated from the body fluid, a suspension for viruses, a suspension containing a body fluid containing viruses or containing viruses separated from the body fluid, and a solution (aqueous solution) in which a filter trapping PM2.5 from the atmosphere or PM2.5 extracted from the filter is dissolved.

A microparticle sample may be obtained by subjecting the sample as described above to pretreatment according to the type of measured spectrum to be acquired, an intended use of spectral data, or the like. For example, a microparticle sample may be subjected to treatment for marking with a fluorescent substance by using molecules or the like at the surface of microparticles for detection by fluorescence. To bind or adsorb a particle with a measurement substrate or the inside of the through-hole, molecules at the surface of a microparticle may be modified with reactive molecules.

(Number n of Microparticles in Microparticle Sample)

A microparticle sample is ordinarily a sample containing a large amount of microparticles and can be a sample containing, for example, microparticles of about the second power of 10 to about the fifteenth power of 10. In the generation method for spectral data of a microparticle according to the present invention, a measured spectrum is obtained from each of n microparticles that correspond to all or some of microparticles contained in the sample. n can be determined according to the amount (number) of microparticles contained in the sample, an intended use of spectral data, or the like. n can be greater than or equal to two, greater than or equal to three, greater than or equal to four, greater than or equal to five, greater than or equal to 10, greater than or equal to 20, greater than or equal to 30, greater than or equal to 40, greater than or equal to 50, greater than or equal to 60, greater than or equal to 70, greater than or equal to 80, greater than or equal to 90, greater than or equal to 100, or the like. It is possible to make an analysis with statistical processing by using spectral data made up of n measured spectra obtained with the generation method according to the present invention. When unidentified microparticles are measured, an analysis with a further high reliability is possible by using greater n (preferably greater than 100) pieces of spectral data. On the other hand, when particles with known spectral characteristics are measured, an analysis with a high reliability is also possible with n less than or equal to five. By obtaining a measured spectrum from each of a plurality of microparticles, it is possible to obtain further accurate information on microparticles, and it is possible to detect characteristics exhibited in only some of microparticles in the sample. There is no upper limit of n. In consideration of time and work for acquiring measured spectra and processing of data, n can be 1000 or less, 500 or less, 300 or less, or the like.

(Measured Spectrum)

In the generation method for spectral data of a microparticle sample according to the present invention, a measured spectrum is obtained from each of the n microparticles. One or more measured spectra can be measured per one microparticle. The number of spectra measured per one microparticle is preferably the same, and one measured spectrum is preferably obtained per microparticle. In other words, spectral data obtained with the generation method for spectral data of a microparticle sample according to the present invention is preferably a bundle of n measured spectra.

The bundle of n measured spectra obtained with the generation method for spectral data of a microparticle sample according to the present invention is a bundle of n measured spectra shown in two or more dimensions. A bundle of n measured spectra means a collection of n measured spectra and does not mean a spectrum obtained by accumulating n measured spectra or a spectrum obtained by averaging n measured spectra. However, the bundle of n measured spectra may be accumulated or averaged and used where necessary. A bundle of n measured spectra may be the one (for example, a matrix, a heat map, or a waterfall plot) obtained by subjecting n measured spectra shown in two or more dimensions to data processing.

A measured spectrum is not limited and may be a spectrum that can give a result based on one microparticle. Examples of the measured spectrum include a Raman spectrum, an infrared spectrum, a fluorescent spectrum, and a mass spectrum. A measured spectrum is preferably a Raman spectrum or a fluorescent spectrum, and a Raman spectrum is particularly preferable.

(Method of Obtaining Measured Spectrum)

The generation method for spectral data of a microparticle sample according to the present invention includes obtaining a measured spectrum from each of n microparticles in a microparticle sample. A method of obtaining a measured spectrum from a microparticle is not limited. For example, preferably, an external stimulus is applied to a microparticle according to a measured spectrum to be acquired, and a microparticle-derived signal is measured. For example, to acquire an infrared spectrum, infrared light is applied, and absorption of irradiated light according to a wave number is observed. To acquire a fluorescent spectrum, single-color excitation light is applied, and fluorescence generated is observed. To acquire a mass spectrum, electron beam irradiation, ion irradiation, laser irradiation, or the like needed to ionize molecules is performed.

The type of external stimulus depends on a measured spectrum to be acquired as described above and is preferably light. The light is preferably laser light. This is because a laser light has high directivity and high light-condensing property and is suitable for measurement of microparticles with a length of 10 nm to 5 μm. As for the laser light, laser with a necessary wavelength may be selected and used from among semiconductor laser, gas laser, solid laser, and the like.

Single-color laser light can be applied to acquire a Raman spectrum. When single-color light with a constant frequency is applied to a substance, a majority of scattered light generated has the same frequency as incident light; however, an extremely small amount of scattered light (Raman scattered light) with a different frequency is generated. A difference (Raman shift) between the frequency of the scattered light and the frequency of incident light corresponds to a vibrational state of molecules that make up the substance. Therefore, a Raman spectrum obtained by plotting the intensity of Raman scattered light in relation to a Raman shift is used as an analysis method for learning the structure and state of molecules that make up the substance.

The wavelength of monochromatic light used to acquire a Raman spectrum may be selected from among wavelengths obtained by using known light sources that apply extraneous light (excitation light) with wavelengths, which can generate Raman scattered light. For example, the wavelength may be selected as needed in the range of about 400 nm to about 800 nm according to a microparticle to be analyzed and a component contained in the microparticle. Because a Raman spectrum allows near infrared light that has less influence on a biological sample to be used as excitation light, it is possible to observe cells alive under a culture condition.

Raman scattered light from a component contained in a microparticle is extremely weak, so the Raman scattered light is preferably enhanced. Examples of the method of enhancement include resonant Raman scattering, tip-enhanced Raman scattering (TERS), and surface-enhanced Raman scattering (SERS). These techniques may be combined. The techniques are known. For example, it is known that, when surface-enhanced Raman scattering is obtained by causing a metal that exhibits plasmon resonance, such as gold and silver, to adsorb molecules, the intensity of scattered light can be enhanced by 104 (the fourth power of 10) times or more as compared to Raman scattered light from isolated molecules. When a measured spectrum is acquired by using the substrate according to the present invention, having a through-hole of which the inner surface is a metal that exhibits plasmon resonance, an enhancing effect at least based on surface-enhanced Raman scattering is obtained, and, furthermore, when the through-hole has a predetermined shape, it is possible to obtain $10^8$ (the eighth power of 10) times enhancement. The external stimulus in the case of using the substrate is not limited as long as the external stimulus is a stimulus that induces plasmon resonance. It is preferable to use single-color laser used at the time of measuring a Raman spectrum.

Examples of the method of obtaining a measured spectrum from each of n microparticles of a microparticle sample containing a plurality of microparticles (preferably, a generation method for the Raman spectrum of a microparticle) include as follows.

Initially, there is a method of obtaining a measured spectrum of each microparticle under microscope observation by spraying microparticles in a sample onto a substrate used at the time of measuring a spectrum and scanning with a probe, such as a light irradiator and a detector. Alternatively, similarly, a measured spectrum of each microparticle can be obtained by spraying microparticles in a sample on a substrate used at the time of measuring a spectrum and scanning the substrate. When the measured spectrum is a Raman spectrum, a probe that induces plasmon resonance is preferably used as a probe.

There is a method of acquiring a measured spectrum of each microparticle while moving the microparticles in a substantially horizontal direction with a means of electrophoresis or optical tweezers under microscope observation on the substrate used at the time of measuring a spectrum. When, for example, the measured spectrum is a Raman spectrum or a fluorescent spectrum, a substrate provided with a through-hole of which at least the surface is a metal that exhibits plasmon resonance is preferably used. This is because it is possible to obtain surface-enhanced Raman scattered light or fluorescence enhancement due to plasmon resonance (surface plasmon-field enhanced fluorescence) by holding a microparticle at the location of the through-hole through adsorption or the like and acquiring a measured spectrum. It is possible to obtain a measured spectrum from each of n microparticles by repeating this procedure.

Furthermore, there is a method of obtaining a measured spectrum of each microparticle while moving the microparticles in a sample one by one in a substantially normal direction of the substrate. For example, it is possible to cause microparticles to pass through a through-hole of the substrate having the through-hole one by one with a means of electrophoresis or optical tweezers and to measure the microparticle at the location of the through-hole. With this procedure, it is possible to further early, further simply obtain a large number of measured spectra. When, for example, the measured spectrum is a Raman spectrum or a fluorescent spectrum, a substrate of which at least the inner surface of the through-hole is a metal that exhibits plasmon resonance is preferably used. This is because it is possible to obtain surface-enhanced Raman scattering or surface plasmon-field enhanced fluorescence by acquiring a measured spectrum inside the through-hole. It is possible to obtain a measured spectrum from each of n microparticles by repeating this procedure.

In the method of obtaining a measured spectrum from each of n microparticles of a microparticle sample containing a plurality of microparticles, it is preferable to acquire a measured spectrum in a state where the substrate is fixed from the viewpoint of obtaining a larger number of measured spectra earlier, simpler. In comparison with the method of acquiring a Raman spectrum from cells one by one by moving a sample holding section at paragraphs [0035] to [0036] in PTL 2, it is possible to acquire a measured spectrum earlier by acquiring a measured spectrum in a state where the substrate is fixed. Furthermore, the light irradiator and the detector are also preferably fixed.

Furthermore, it is more preferable to acquire a Raman spectrum or a fluorescent spectrum with the procedure including applying light from a surface side having a larger opening portion of the through-hole from the viewpoint of further enhancing the intensity of Raman scattered light or the intensity of fluorescence.

<Analysis Method for Microparticle>

An analysis method for a microparticle according to the present invention includes making a statistical analysis of spectral data acquired by the generation method according to the present invention. It is possible to make an analysis based on components contained in a microparticle by making a statistical analysis of spectral data obtained with the generation method for spectral data of a microparticle sample according to the present invention, that is, a bundle of n measured spectra (a new database obtained in the present invention). A statistical analysis may be made by using machine learning or artificial intelligence (AI). When an analysis of an unidentified microparticle is made by using a statistical analysis, n at the time of performing the generation method according to the present invention to obtain sufficient accuracy and reliability (when a new database obtained in the present invention is constructed) is preferably greater than or equal to 20, more preferably greater than or equal to 50, further preferably greater than or equal to 80, and particularly preferably greater than or equal to 100. On the other hand, when an analysis of known microparticles or using known particles is made, sufficient reliability may be obtained even when n at the time of performing the generation method according to the present invention (at the time of constructing a new database obtained in the present invention) is small, that is, for example, two to five.

(Multivariate Analysis)

An example of a preferred mode of the analysis method according to the present invention is an analysis method including making a multivariate analysis on n measured spectra of spectral data acquired with the generation method according to the present invention, and identifying at least one component contained in a microparticle by comparing a spectrum, obtained through the multivariate analysis, with spectra of known substances.

As for spectral data, information based on a component of a microparticle can be obtained by, for example, making a principal component analysis, a sparse principal component analysis, non-negative matrix factorization (multivariate curve resolution-alternating least squares), a cluster analysis, an independent component analysis, a linear discriminant analysis, a logistic regression analysis, or a multivariate analysis, such as Gaussian mixture model.

Since a bundle of measured spectra for microparticles one by one is obtained with the generation method for spectral data of a microparticle according to the present invention, it is possible to obtain information on a component contained by using the analysis method as described above.

When, for example, information on a constituent component of a measurement microparticle is known, it is possible to make a detailed analysis by making an analysis using spectral data of the known constituent component (known spectral database) on a new database obtained in the present invention. Furthermore, determination as to whether a specific component is present in a microparticle (for example, a marker molecule of a cancer or the like) can be performed by making an analysis based on a spectrum of the specific component.

It is possible to obtain information on a component contained even for an unidentified microparticle by using the analysis method as described above. It is possible to identify a component contained in a microparticle by, for example, making a principal component analysis on spectral data generated with the generation method according to the present invention and comparing the obtained spectrum of the principal component with known spectra (for example, a known spectral database can be used).

(Analysis Using Correlation Coefficient)

An analysis using a correlation coefficient is another example of the analysis method for a microparticle. Specifically, it is possible to identify a component contained in a microparticle by forming a set of peaks having a mutually high correlation coefficient between n measured spectra generated with the generation method according to the present invention and comparing the obtained set of peaks with spectra of known substances (for example, a known spectral database can be used). A set of peaks may be any set including two or more peaks. For example, a set of peaks may consist of only two peaks (for example, two characteristic peaks of components) or may correspond to a spectrum.

In other words, when peak A increases, peak B increases by the same amount at the same time, the correlation coefficient between A and B is 1, the correlation coefficient is 0 when the peak B does not change, and, conversely, when both reduce by the same amount, the correlation coefficient between peak A and peak B is-1. In the case of Raman spectrum, a peak corresponds to a molecule, and, as the correlation coefficient increases, those peaks can be determined as signals from the same molecules. The correlativity is checked for all the obtained data, that is, a correlation coefficient is obtained between spectra for peaks receiving attention among n spectra. Thus, synchronous peaks are found. The peaks that synchronize with each other can be determined as signals from the same molecules.

[As for a specific procedure, spectra of particles are used to form an N-by-M matrix as shown in Table 1. After that, a correlation coefficient in intensity at each of two wave number points (Yth and Y'th) is calculated based on the expression specifically shown in the embodiment. A correlation coefficient may be obtained after the maximum value of each spectrum is normalized to one or subjected to general standardization processing or both as needed.

TABLE 1

| | First Raman Shift Wave Number (Y or Y' = 1) | Second Raman Shift Wave Number (Y or Y' = 2) | Third Raman Shift Wave Number (Y or Y' = 3) | . . . | Mth Raman Shift Wave Number (Y or Y' = M) |
|---|---|---|---|---|---|
| Spectrum of Particle 1 | Intensity $X_{1\cdot1}$ | Intensity $X_{1\cdot2}$ | Intensity $X_{1\cdot3}$ | . . . | Intensity $X_{1\cdot M}$ |
| Spectrum of Particle 2 | Intensity $X_{2\cdot1}$ | Intensity $X_{2\cdot2}$ | Intensity $X_{2\cdot3}$ | . . . | Intensity $X_{2\cdot M}$ |
| Spectrum of Particle 3 | Intensity $X_{3\cdot1}$ | Intensity $X_{3\cdot2}$ | Intensity $X_{3\cdot3}$ | . . . | Intensity $X_{3\cdot M}$ |
| . | . | . | . | . | . |
| . | . | . | . | . | . |
| . | . | . | . | . | . |
| Spectrum of Particle N | Intensity $X_{N\cdot1}$ | Intensity $X_{N\cdot2}$ | Intensity $X_{N\cdot3}$ | . . . | Intensity $X_{N\cdot M}$ |

<Determination Method of Determining Presence or Absence of Cancer Cell-Derived Exosome in Body Fluid-Derived Sample Containing Exosomes>

An analysis of the presence or absence of a specific microparticle using a signal based on a partial structure of a component that exhibits the properties of a microparticle is also possible through an analysis using a correlation coefficient.

The determination method according to the present invention is a determination method of determining presence or absence of a cancer cell-derived exosome in a body fluid-derived sample containing exosomes. The determination method according to the present invention includes generating spectral data including n measured spectra respectively obtained from n exosomes in the sample with the generation method according to the present invention, obtaining a correlation coefficient between a signal having a local maximum at 1087 $cm^{-1\pm5}$ $cm^{-1}$ and a signal having a local maximum at 1435 $cm^{-1\pm5}$ $cm^{-1}$ between the n measured spectra, and determining that a cancer cell-derived exosome is present in the sample when the correlation coefficient is higher than or equal to a certain value.

In the embodiment, the presence of phosphorylated protein is identified by acquiring 155 measurement Raman spectra for exosomes in a body fluid-derived sample containing exosomes and checking a correlation between two characteristic signals due to a structure in phosphoserine among the obtained spectra. Specifically, the presence of phosphorylated protein is identified based on the fact that a signal having a local maximum at 1087 $cm^{-1=5}$ $cm^{-1}$ and a signal having a local maximum at 1435 $cm^{-1\pm5}$ $cm^{-1}$ synchronize with each other, that is, the correlation coefficient is higher than or equal to a certain value. Phosphoserine is a characteristic partial structure of phosphorylated protein, and the presence of phosphorylated protein is the characteristic of a cancer cell-derived exosome (NPL 4). Therefore, it is possible to determine the presence or absence of a cancer cell-derived exosome in the sample based on the presence or absence of synchronization of the signals. The determined result can be used for a diagnosis of a cancer.

[NPL 4] Shilian Dong et al., "Beehive-Inspired Macroporous SERS Probe for Cancer Detection through Capturing and Analyzing Exosomes in Plasma", ACS Appl. Mater. Interfaces, Vol. 12, pp. 5136-5146.

An analysis using a correlation coefficient can be made by using two-dimensional mapping of spectra as shown in the embodiment.

<Discrimination Method of Discriminating Yet-to-be Discriminated Microparticle>

Furthermore, it is possible to make an analysis of a yet-to-be discriminated (unidentified) microparticle by using spectral data of known microparticles acquired with the generation method according to the present invention. For example, it is possible to perform discrimination of microparticles of the same species (for example, viruses and exosomes) but the microparticles have mutually different properties or the like (for example, discrimination of a displacive type virus, discrimination of a specific disease, such as a cancer, patient-derived microparticle, or the like).

In an example, with the result that a principal component analysis is made by using a bundle of measured spectra, obtained by adding up bundles of measured spectra acquired with the generation method according to the present invention respectively for mutually different microparticle samples, when an index that discriminates mutually different microparticles is found, it is possible to perform discrimination of microparticles by using the index.

Among discriminations of microparticles using spectral data of known microparticles, acquired with the generation method according to the present invention, discrimination is preferably applied to a discrimination method according to the present invention, which will be described below.

The discrimination method according to the present invention is a discrimination method of discriminating a yet-to-be discriminated microparticle. The discrimination method includes:

acquiring $N_A$ measured spectra of microparticles A of which a type is identified and $N_B$ measured spectra of microparticles B of which another type is identified, with the generation method according to the present invention;

obtaining an index that discriminates the measured spectra of microparticle A and microparticle B from scores of two or more principal components by making a principal component analysis of spectral data including $N_A+N_B$ measured spectra;

obtaining a measured spectrum of each of one or more yet-to-be discriminated microparticles in a microparticle sample;

calculating scores of two or more principal components of the measured spectrum of the yet-to-be discriminated microparticle; and performing discrimination by comparing the scores of the yet-to-be discriminated microparticle with the index. A length of the yet-to-be discriminated microparticle ranges from 10 nm to 5 μm.

A conceivable index used in a case of discriminating whether an intended sample microparticle (yet-to-be discriminated microparticle) is microparticle A (known sample microparticle 1) or microparticle B (known sample microparticle 2) will be described below.

Spectral data that is a bundle of $N_1+N_2$ measured spectra is obtained by adding up a bundle of $N_1$ measured spectra of sample microparticles 1 and a bundle of $N_2$ measured spectra of sample microparticle 2. An index for discriminating measured spectra of sample microparticle 1 and sample microparticle 2 is obtained from scores of two or more principal components by making a principal component analysis of spectral data including the $N_1+N_2$ measured spectra. $N_1$ and $N_2$ each are preferably greater than or equal to 20, more preferably greater than or equal to 50, and further preferably greater than or equal to 100. In a specific example, data points of each spectrum are defined as MM points, and a matrix of $(N_1+N_2)\times$ MM is generated. When, for example, the number of spectra in each of the bundle of spectra of sample microparticles 1 and the bundle of spectra of sample microparticles 2 is 100 and the data points of each spectrum are 1000 points, a matrix of 200×1000 is obtained from the added-up 200 spectra in the spectral bundle. A variance-covariance matrix for this matrix is obtained, and, furthermore, eigenvalues and eigenvectors for the variance-covariance matrix are obtained. At this time, normalization and standardization of the spectral bundle may be performed as needed. The eigenvalues are defined as a first principal component and a second principal component in order from a larger one, and a score plot is generated by using an eigenvector at each eigenvalue. When score plots of two or more principal component scores, that is, for example, the first principal component and the second principal component, are formed and a boundary line can be formed between the microparticles, this can be set for the above-described index.

In other words, it is possible to discriminate a yet-to-be discriminated microparticle by calculating the scores of the principal components for a measurement-target spectrum acquired from the yet-to-be discriminated microparticle and comparing the scores with the score plots. A measurement-target spectrum may be a measured spectrum of a microparticle or may be spectral data generated with the generation method according to the present invention.

A preferred mode in a case where spectral data of a yet-to-be discriminated microparticle is acquired as a measured spectrum of a microparticle is similar to a preferred mode of the generation method according to the present invention. When a yet-to-be discriminated microparticle is acquired as a measured spectrum of a microparticle, it is preferable to acquire a measured spectrum of a microparticle by using the substrate for measuring a spectrum of a microparticle according to the present invention.

(Discrimination Method of Discriminating Whether Target Exosome is Derived from Cancer Cell)

Among the discrimination methods of discriminating a yet-to-be discriminated microparticle, the discrimination method according to the present invention is a discrimination method of discriminating whether a target exosome is derived from a cancer cell. The discrimination method preferably includes:

acquiring $N_1$ measured spectra of cancer cell-derived exosomes and $N_2$ measured spectra of normal cell-derived exosomes, with the generation method according to the present invention;

obtaining an index for discriminating a cancer cell-derived measured spectrum and a normal cell-derived measured spectrum from scores of two or more principal components by making a principal component analysis of spectral data including $N_1+N_2$ measured spectra;

calculating scores of two or more principal components of a spectrum of the target exosome; and performing discrimination by comparing the scores of the target exosome with the index.

Other preferred modes of the discrimination method may be modes, that is, a discrimination method, a learning method, a discrimination apparatus, and the like that use a microparticle with a length less than or equal to 5 μm instead of a cell at paragraphs to [0085] of PTL 2. The contents described at the paragraphs of PTL 2 are incorporated by reference in the specification.

Specifically, it is preferable to discriminate a type of yet-to-be discriminated microparticle by acquiring a measured spectrum (for example, a Raman spectrum or a fluorescent spectrum) from the yet-to-be discriminated microparticle, calculating a plurality of degrees of coincidence each indicating a degree to which the measured spectrum of the yet-to-be discriminated microparticle coincides with a corresponding one of spectra of a plurality of principal components, obtained through a principal component analysis of a plurality of measured spectra that are measured spectra obtained one by one respectively from a plurality of microparticles of which types are identified, classifying the plurality of degrees of coincidence based on a result that a plurality of principal component scores respectively corresponding to the plurality of microparticles of which the types are identified and which are obtained through the principal component analysis are classified by types with a learning model that uses supervised learning.

A support vector machine is preferably used as a learning model that uses supervised learning. Another learning model may be used. It is preferable to perform machine learning of a learning model, such as a support vector machine, by using a plurality of principal component scores respectively corresponding to a plurality of microparticles of which types are identified and the types of the microparticles as supervised data. A discrimination apparatus that performs discrimination of a type of microparticle preferably acquires supervised data from an outside source.

On the other hand, classification may be performed by using a learning model that uses unsupervised learning, and a learning model that uses unsupervised learning may be clustering or the like.

The discrimination apparatus preferably acquires, from an outside source, spectra of a plurality of principal components, obtained through a principal component analysis of a plurality of measured spectra from a plurality of microparticles of which types are identified and a result that a plurality of principal component scores respectively corresponding to the plurality of microparticles of which the types are identified are classified by types with a learning model.

At the time of classifying a plurality of principal component scores respectively corresponding to a plurality of microparticles of which types are identified, a coordinate space in which coordinate points having the plurality of principal component scores as components are included is preferably divided into a plurality of regions by a learning model, such as a support vector machine. For example, each coordinate point is a two-dimensional coordinate point having a first principal component score and a second principal component score as components. In response to division of the coordinate space, the plurality of principal component scores is classified by the type of microparticle.

(Discrimination Method Through Comparison in Two-Dimensional Mapping of Correlation Coefficients)

It is also possible to discriminate a measurement-target unidentified microparticle by comparing two-dimensional mapping of correlation coefficients, obtained as described above in relation to known microparticles, with two-dimensional mapping of correlation coefficients, similarly obtained in relation to the measurement-target unidentified microparticle, and determining whether different or the same.

<Substrate for Measuring Spectrum of Microparticle>

The substrate for measuring a spectrum of a microparticle according to the present invention has a through-hole that extends through from one surface of the substrate to the other surface of the substrate. The through-hole has a size such that the microparticle can pass through one by one. At least part of an inner surface of the through-hole is made of a metal that exhibits plasmon resonance. The through-hole has a tapered structure in which a width continuously reduces from one surface of the substrate toward the other surface of the substrate. As described above, when the substrate having the through-hole is used to obtain a measured spectrum from each of n microparticles of a sample containing a plurality of microparticles, it is possible to earlier, more easily obtain a large amount of measured spectra. Hereinafter, the substrate for measuring a spectrum of a microparticle according to the present invention, having such a through-hole, will be described.

The substrate for measuring a spectrum of a microparticle according to the present invention is applicable to a microparticle with a length that ranges from 10 nm to 5 μm, a particle with a length greater than that range, and a microparticle with a length less than that range. However, the substrate for measuring a spectrum of a microparticle according to the present invention is preferably applied to a microparticle with a length that ranges from 10 nm to 5 μm. Particularly, the generation method for spectral data of a microparticle sample according to the present invention, the analysis method for a microparticle according to the present invention, or the discrimination method according to the present invention is performed more preferably by applying the substrate for measuring a spectrum of a microparticle according to the present invention to a microparticle with a length that ranges from 10 nm to 5 μm.

(Substrate)

A substrate is not limited as long as the substrate can be used at the time of measuring a spectrum. A sheet-like substrate can be used as the substrate. Examples of the material of the substrate include inorganic materials and organic materials, such as polymer materials. The material of the substrate preferably has electrical insulating properties. Examples of the material of the substrate are not limited to electrically insulating materials used in the field of semiconductor manufacturing technology, such as silicon (silicon: Si), and include glass, quartz, gold, silver, copper, aluminum, polydimethylsiloxane (PDMS), polytetrafluoroethylene (PTFE), polystyrene, and polypropylene. The thickness of the substrate is not limited as long as a through-hole can be provided. For example, the thickness can range from about 50 nm to about 1 mm, preferably ranges from 50 nm to 500 μm, and more preferably ranges from 1 μm to 500 μm. The size of the substrate is not limited as long as a through-hole can be provided.

The substrate can be manufactured with a known method, and a commercial item may be used. The through-hole can be formed with known means, such as etching and photolithography. The entire surface or part of the surface (for example, a part inside or near the through-hole) of the substrate may be surface treated.

(Through-Hole)

The substrate has a through-hole that extends through from one surface of the substrate to the other surface of the substrate. The size of the through-hole is set such that measurement-target microparticles can pass through one by one. Therefore, the size of the through-hole can be adjusted as needed so as to be greater than a maximum sectional area at the time of passage of a microparticle intended to be detected but not too large. For example, an equivalent circle diameter of the through-hole can range from 10 nm to 5 μm. When the measurement-target microparticle is an exosome, the equivalent circle diameter of the through-hole can range from 50 nm to 4 μm at the smallest part. In the specification, the equivalent circle diameter of the through-hole means the diameter of a circle with an area equal to the sectional area of a cross section (a cross section parallel to one surface or the other surface) of the through-hole.

The shape of the through-hole is not limited and is, for example, a frustum, such as a cone frustum and a pyramid frustum. The shapes of two bases (an upper base and a lower base) of the frustum are ordinarily similar and may be not necessarily similar. For example, one base of the frustum may be a square, and the other base may be a rectangle. It is preferable to select the shape and width of the through-hole according to the wavelength of laser used and the refractive index near the through-hole. When, for example, 785 nm laser is used in an aqueous solution, a through-hole having any one of the above-described shapes may be provided in a range in which the equivalent circle diameter of an opening portion of the through-hole at any one surface of the substrate ranges from 10 nm to 5 μm (preferably ranges from 50 nm to 3 μm, more preferably ranges from 50 nm to 1 μm, particularly preferably ranges from 50 nm to 500 nm, and further particularly preferably ranges from 100 nm to 200 nm) and the equivalent circle diameter of an opening portion of the through-hole at the other surface ranges from 10 nm to 500 μm (preferably ranges from 50 nm to 1 μm). The through-hole preferably has a shape having a tapered structure such that a width of the through-hole continuously reduces from one surface of the substrate to the other surface of the substrate. At this time, the equivalent circle diameter of the through-hole at the surface in which the sectional area of the through-hole is maximum is preferably greater than or equal to 500 nm. The equivalent circle diameter of the through-hole at the surface in which the sectional area of the through-hole is minimum is preferably greater than or equal to 50 nm, and more preferably greater than or equal to 100 nm and less than or equal to 1 μm.

Preferably, the substrate for measuring a spectrum of a microparticle has a through-hole that extends through from one surface of the substrate to the other surface of the substrate as described above, the through-hole has a size such that microparticles can pass through one by one, at least an inner surface of the through-hole is a metal that exhibits plasmon resonance, and the through-hole has a shape (tapered structure) so as to continuously reduce from one surface of the substrate to the other surface of the substrate. Hereinafter, the substrate for measuring a spectrum of a microparticle of the preferred mode may be referred to as the substrate according to the present invention. The inventors found that sensitivity enhanced $10^8$ (the eighth power of 10) times was shown when the substrate according to the present invention was particularly used to measure a Raman spectrum as compared to measurement at the time when the substrate was not used (when the substrate having a cylindrical through-hole is used). Since the through-hole has a shape (tapered structure, preferably, a shape of a quadrangular pyramid frustum) that a width continuously reduces from one surface of the substrate to the other surface of the substrate, incident light gathers along the tapered structure to the through-hole at the surface where the width of the through-hole is minimum, and incident light can be efficiently used. This is one of the reasons that the degree of enhancement is obtained. The degree of enhancement is equivalent to a value generally defined as an enhancement factor (EF) in surface enhanced Raman spectroscopy. The degree of enhancement is a value obtained by measuring 4-aminothiophenol molecules (Sigma-Aldrich Co. LLC) generally used as a reference sample in Raman spectroscopy and measuring how many times Raman scattered light is enhanced with the presence of the through-hole.

It is possible to continuously obtain a measured spectrum of each microparticle by causing microparticles one by one through the through-hole of the substrate according to the present invention and measuring the microparticle at the location of the through-hole. With the generation method for spectral data for measuring a Raman spectrum with the substrate according to the present invention, even without a marker of fluorescent molecules or the like, immobilization to a metal surface, or the like, it is possible to efficiently acquire spectral data obtained through high-sensitivity measurement.

The shape of a quadrangular pyramid frustum is particularly preferable as the shape of the through-hole of the substrate according to the present invention. An angle that the inner surface (the trapezoidal lateral face in the case of the shape of a quadrangular pyramid frustum) of the through-hole in the substrate according to the present invention makes with the surface of the substrate preferably ranges from 30 degrees to 90 degrees, more preferably ranges from 30 degrees to 60 degrees, and particularly preferably exceeds 45 degrees and is less than or equal to 60 degrees.

In the substrate according to the present invention, at least the inner surface of the through-hole is a metal that exhibits plasmon resonance. The material of the substrate according to the present invention is preferably a metal that exhibits plasmon resonance. Examples of the metal that exhibits plasmon resonance include metals, such as gold, silver, copper, and aluminum, and combinations of two or more of them. The metal that exhibits plasmon resonance is preferably gold or silver and more preferably gold.

From the viewpoint of easiness of forming the through-hole or the viewpoint of cost, the substrate according to the present invention may have a base material made of an electrically insulating material generally used in the field of semiconductor manufacturing technology and has a layer of a metal that exhibits plasmon resonance on at least the inner surface of the through-hole of the base material. Examples of the electrically insulating material that can be used as the base material include Si, Ge, Se, Te, GaAs, GaP, GaN, InSb, InP, $Si_3N_4$ (silicon nitride), $SiO_2$ (silicon dioxide), and combinations of any two or more of them. Among these, Si is preferable as the base material, and a base material main body is more preferably made of Si. As in the case of the base material used in the embodiment, a material having an $Si_3N_4$ layer or an $SiO_2$ layer is preferably used for the surface of a sheet-like base material main body made of Si.

The through-hole in the substrate according to the present invention can be formed by, for example, etching, or the like. A preferable method of forming the through-hole is a manufacturing method of forming the through-hole into a shape of a quadrangular pyramid frustum by etching in the substrate for measuring a spectrum of a microparticle according to the present invention. Specifically, a manufacturing method for the substrate according to the present invention, described below, is preferable.

The manufacturing method for the substrate according to the present invention includes forming a hole having a quadrangular pyramid shape through anisotropic etching with wet etching from one surface of the base material including the base material main body made of Si and forming a through-hole by causing the hole to extend through with wet etching at an opposed location at the other surface of the base material. An example of the procedure is described in the embodiment (described later). In the embodiment, a quadrangular pyramid-shaped hole is formed by anisotropic wet etching from one surface of a silicon wafer (sheet-like base material made of Si) and then wet etching is performed from the other surface at an opposed location. When the through-hole is formed with the manufacturing method, it is possible to cause the hole to extend through and adjust the size of the opening portion to a preferable range. The size of the opening portion can be adjusted to a desired size after a layer of a metal that exhibits plasmon resonance is formed.

In the substrate according to the present invention, the layer of a metal that exhibits plasmon resonance, provided on at least the inner surface of the through-hole of the base material, may be formed only on the inner surface of the through-hole, may be additionally formed on any one surface of the base material, and may be additionally formed on both surfaces of the base material. The layer of a metal that exhibits plasmon resonance can be formed on the surface of the base material with means, such as vapor deposition.

In the substrate according to the present invention, the thickness of the layer of a metal that exhibits plasmon resonance, provided on at least the inner surface of the through-hole of the base material, can be greater than or equal to 50 nm and is preferably greater than or equal to 50 μm. Because it is preferable that the thickness is greater, there is no particular upper limit; however, from the viewpoint of easiness and cost of manufacturing, the thickness is preferably less than or equal to 100 μm.

In the substrate according to the present invention, the sectional shape of the opening portion of the through-hole at any one surface of the substrate is preferably a quadrangle with sides of 10 nm to 5 μm. In the substrate according to the present invention, the width of the through-hole at any one opening portion of the substrate where the width of the through-hole is minimum preferably ranges from 50 nm to 500 nm and more preferably ranges from 100 nm to 500 nm. Particularly, this part preferably has a quadrangle with the sides of 50 nm to 5 μm by 50 nm to 5 μm, more preferably has a quadrangle with the sides of 100 nm to 5 μm by 100 nm to 5 μm, and further preferably has a quadrangle with the sides of 100 nm to 500 nm by 50 nm to 500 nm. At this time, the thickness of the substrate preferably ranges from 50 μm to 500 μm. With the substrate of this size, it is possible to efficiently measure particularly an exosome, specifically, an exosome with a particle diameter of about 50 nm to about 150 nm, with high sensitivity.

The sectional shape of the opening portion of the through-hole may have a short axis and a long axis. The ratio (aspect ratio) of the length (long axis) of the sectional shape of the opening portion of the through-hole to the width (short axis) of the opening portion may, for example, range from 99:1 to 50:50, preferably ranges from 90:10 to 50:50, and more preferably ranges from 80:20 to 50:50. The sectional shape of the opening portion of the through-hole is preferably a rectangle among quadrangles. A preferred example of the sectional shape of the opening portion of the through-hole is, for example, a rectangle of 100 nm×300 nm (aspect ratio 76:24).

(Acquisition Method for Measured Spectrum Using Substrate Having Through-Hole)

—Adjusting Microparticle to State Dispersed in Liquid—

When measurement of a spectrum is performed by using the substrate having the through-hole, a microparticle is preferably adjusted to a state dispersed in a liquid. This is because it is easy to guide a microparticle to the through-hole and cause the microparticle to pass through the through-hole. An electrolytic solution is preferable as a liquid in which a microparticle is dispersed. The electrolytic solution is not limited. The electrolytic solution is preferably a solution that an ionic substance is dissolved in a polar solvent. Examples of the electrolytic solution include TE buffer (Tris-EDTA buffer: made by Nippon Gene Co., Ltd.).

—Causing Microparticle to Pass through Through-Hole-Causing—

Causing a microparticle to pass through the through-hole preferably includes guiding a microparticle to pass through the through-hole preferably includes guiding a microparticle into the through-hole or to near the through-hole, holding the guided microparticle inside the through-hole or near the through-hole, and removing the held microparticle from inside the through-hole or near the through-hole. A spectrum can be measured in holding. A location to be held can be inside the through-hole and may be near the through-hole, that is, a part or the like that adjoins the through-hole of the surface of the substrate, according to a microparticle to be measured and the property of spectrum to be measured. However, at the time of measuring a spectrum when a microparticle does not need to be held inside the through-hole or near the through-hole, holding may be omitted. A microparticle preferably enters the through-hole from the opening portion on one surface side of the substrate at the through-hole provided in the substrate and exits from the through-hole through the opening portion on the other surface side of the substrate.

A microparticle can be guided into the through-hole or to near the through-hole by using electrophoresis, dielectrophoresis, optical tweezers, Brownian movement, Coulomb interaction, or the like. In the present invention, a microparticle dissolved in a liquid (electrolytic solution) is preferably caused to pass through the through-hole with one or more methods selected from the group consisting of electrophoresis, dielectrophoresis, optical tweezers, Brownian movement, and Coulomb interaction. A plurality of actions and methods may be combined and used.

A microparticle can be held inside the through-hole or near the through-hole by, for example, being adsorbed into the through-hole or to near the through-hole. Examples of the adsorbing method include a method of, when a biogenic microparticle has a negative charge, adsorbing with Coulomb force by positively charging the through-hole, a method with optical tweezers, and a chemically adsorbing method. The chemically adsorbing method is adsorption using a microparticle and a reactive molecule on the surface of a nanostructure. For this purpose, a part inside the through-hole or near the through-hole may be modified or coated with any one or both in advance. For example, adsorption or the like using an antigen-antibody reaction may be used. For example, a part inside the through-hole or near the through-hole may be modified with a group that binds with antibody of which antigen is a molecule present on the surface of the microparticle and may adsorb the microparticle by using the antibody (see, for example, PTL 3).

[PTL 3] WO 2018/221271

A holding time of a microparticle may be determined according to a microparticle to be measured and the property of a spectrum to be measured and may be selected from, for example, a range of 0.00005 seconds to 100 seconds. An upper limit of a preferred range of the holding time of a microparticle is more preferably shorter than or equal to 10 seconds, particularly preferably shorter than or equal to one second, and further particularly preferably shorter than or equal to 0.1 seconds. As described above, holding may be omitted. For example, measurement may be performed while a microparticle is decelerating inside or near the through-hole as compared to a moving speed of the microparticle to the entrance of the through-hole.

Removal of a microparticle from inside the through-hole or near the through-hole can be performed by discharging or application of reverse bias (in the case of Coulomb force), turning off light (in the case of optical tweezers), or elimination reaction (in the case of chemical adsorption).

Adjustment of the above-described moving microparticle and holding inside the through-hole or near the through-hole can be performed under microscope observation. Under microscope observation, it is possible to perform measurement while checking movement of microparticles one by one. Alternatively, in a technique or the like that uses electrophoresis and optical tweezers together, it is possible to automate the above-described steps accompanied by movement of a microparticle by adjusting the concentration of microparticles in a sample containing microparticles, an electrolytic solution used, the period of on/off state of light, and the like. For example, ionic current flowing through the through-hole reduces due to passage of a microparticle through the through-hole, so timing at which a microparticle passes through the through-hole can be found by observing the ionic current. Therefore, when the ionic current is used as a trigger signal, it is possible to automatically turn on and off measurement. An electrode for observing ionic current may be provided at a side wall of the through-hole or immediately near the through-hole.

—Repetition of Measuring Spectrum—

When a procedure to remove a measured microparticle from inside the through-hole or near the through-hole after measuring a spectrum and then guide the next microparticle into the through-hole or to near the through-hole to perform measurement is repeated, it is possible to efficiently obtain a large number of measured spectra (for example, greater than or equal to 20, greater than or equal to 30, greater than or equal to 40, greater than or equal to 50, greater than or equal to 60, greater than or equal to 70, greater than or equal to 80, greater than or equal to 90, or greater than or equal to 100) based on one microparticle. A time taken until obtaining measured spectra from n microparticles completes preferably ranges from 0.00005 seconds to 100 seconds in terms of an average time per microparticle. An upper limit of a preferred range of a time taken until obtaining measured spectra from n microparticles completes is more preferably shorter than or equal to 10 seconds, particularly preferably shorter than or equal to one second, and further particularly preferably shorter than or equal to 0.1 seconds.

—Acquisition of Measured Spectrum—

A measured spectrum is obtained by detecting a signal that occurs when an external stimulus is applied to a microparticle inside the through-hole or near the through-hole. When the through-hole has a shape having a tapered structure such that a width of the through-hole continuously reduces from one surface (surface A) of the substrate to the other surface (surface B) of the substrate, it is preferable to acquire a measured spectrum with a procedure including applying light from the surface side having the larger opening portion of the through-hole from the viewpoint of further enhancing the intensity of Raman scattered light. In other words, an external stimulus is preferably applied from the surface (surface A) side having the larger opening portion. For example, laser is preferably applied from the surface having the larger opening portion of the through-hole. The size of the opening portion of the through-hole on the side of laser irradiation is preferably greater than a spot diameter of laser.

Detection of a signal for measuring a spectrum is also preferably performed from the surface (surface A) side having the larger opening portion.

At the time of measuring a spectrum, a confocal lens and an objective lens are preferably used in combination with a light source to apply extraneous light from the light source to be focused onto a microparticle inside the through-hole or near the through-hole. A microparticle is preferably measured in a liquid, and the objective lens is preferably of an immersion type. Detection of a signal can also be performed through the objective lens. A distance from the objective lens to the through-hole is preferably the same distance as a working distance of the objective lens. In an apparatus used for measuring a spectrum, to suppress a background signal and obtain a higher S/N, an optical filter, a half mirror, or the like may be used by referring to known technologies.

<Device and Apparatus for Measuring Spectrum of Microparticle>

The substrate according to the present invention or another substrate having a through-hole for measuring a microparticle can be used as a member of a device for measuring a spectrum of a microparticle. For example, the device for measuring a spectrum may be configured to include a substrate, a first liquid tank including an inner wall including at least a portion having a through-hole at one surface of the substrate, and a second liquid tank including an inner wall including at least a portion having the through-hole at the other surface of the substrate. With such a configuration, a microparticle in a liquid sample can be guided into the through-hole or to near the through-hole and caused to pass through the through-hole by using electrophoresis, optical tweezers, or the like as described above.

Particularly, of such configurations, the device for measuring a spectrum of a microparticle using the "substrate for measuring a spectrum of a microparticle according to the present invention" as the substrate is referred to as the device for measuring a spectrum of a microparticle according to the present invention (hereinafter, also referred to as the device according to the present invention). Furthermore, the apparatus for measuring a spectrum of a microparticle can be configured by using the device according to the present invention. The apparatus for measuring a spectrum of a microparticle according to the present invention (hereinafter, also referred to as the apparatus according to the present invention) includes the device according to the present invention, a guiding section for causing a microparticle to pass one by one through the through-hole, a light source, and a detecting section that measures light (signal) that occurs when light from the light source is applied to the microparticle in the through-hole and acquires a measured spectrum. Hereinafter, a preferred mode of the device according to the present invention and a preferred mode of the apparatus according to the present invention will be described.

(First Liquid Tank and Second Liquid Tank)

When a microparticle is measured with the device according to the present invention, the microparticle is guided from the first liquid tank to the through-hole, and, after measurement, moves from the through-hole to the second liquid tank. When the substrate in the device has a through-hole whose width continuously reduces from one surface of the substrate to the other surface of the substrate, the liquid tank on the surface side with a larger opening portion is preferably the first liquid tank, and the liquid tank on the surface side with a smaller opening portion is preferably the second liquid tank.

A member for forming the first liquid tank and a member for forming the second liquid tank each are not limited as long as the member can form a liquid tank that is to be filled with liquid (such as an electrolytic solution). The liquid tank is preferably formed from an electrically and chemically inert material. Examples of the material include glass, sapphire, ceramic, resin, rubber, elastomer, $Si_3N_4$ (silicon nitride), $SiO_2$ (silicon dioxide), and $Al_2O_3$.

The first liquid tank and the second liquid tank can be formed so as to sandwich the substrate, and can be formed such that a microparticle put into the first liquid tank can pass through the through-hole and move to the second liquid tank. The first liquid tank and the second liquid tank each may have a hole for charging or discharging a sample solution or an electrolytic solution and a hole for inserting an electrode and/or a lead for electrophoresis.

The electrode may be made of a known electrically conductive metal, such as silver-silver chloride, aluminum, copper, platinum, gold, silver, and titanium. It is possible to move a microparticle by disposing two electrodes respectively in the first liquid tank and the second liquid tank and applying direct current. An applied voltage can be determined according to a condition, such as the type of microparticle to be moved and may be set, for example, between 0.01 V and 1.5 V.

The electrode disposed in the first liquid tank can be connected to a power supply and a ground via a lead. The electrode disposed in the second liquid tank can be connected to an ammeter and the ground via a lead. A connecting location of the power supply and a connecting location of the ammeter may be interchanged between the first liquid tank side and the second liquid tank side. Alternatively, the power supply and the ammeter may be provided at the same electrode side.

The power supply is not limited as long as the power supply can pass direct current between the electrodes. The ammeter is not limited as long as the ammeter can measure ionic current generated with time when current is passed. A noise reduction circuit, a voltage stabilizer, or the like may be provided as needed.

Measurement of a spectrum of a microparticle can be performed by an apparatus including a means (light source) for applying an external stimulus to a microparticle and a means (detecting section) that detects a signal. When measurement of a spectrum of a microparticle is performed with the substrate having the through-hole, the apparatus preferably further includes a means (guiding section) for causing a microparticle to pass one by one through the through-hole.

(Means (Light Source) for Applying External Stimulus to Microparticle)

The means for applying an external stimulus to a microparticle is a light source. A preferred light source is laser. When the measured spectrum is a Raman spectrum or a fluorescent spectrum, the means for applying an external stimulus to a microparticle can be a laser light source.

The apparatus according to the present invention preferably includes an inlet for causing the laser light to irradiate the through-hole.

(Means for Detecting Signal (Detecting Section))

The detecting section that detects a signal, for example, acquires a measured spectrum by measuring light that occurs as a result of an external stimulus. Light that occurs as a result of an external stimulus is Raman scattered light, fluorescence, or the like that occurs when light from the laser light source is applied to a microparticle. The detecting section includes, for example, a spectroscope for dispersing light and a detector (photo receiving apparatus) for detecting light. The detecting section more preferably includes a spectroscope for dispersing Raman scattered light and a detector for detecting the dispersed Raman scattered light. Furthermore, in the apparatus according to the present invention, more preferably, the measured spectrum is a Raman spectrum, the light source is a laser light source, and the detecting section includes a spectroscope for dispersing Raman scattered light and a detector for detecting the dispersed Raman scattered light.

(Means for Causing Microparticle to Pass One by One Through Through-Hole (Guiding Section))

A means for causing a microparticle to pass one by one through the through-hole is not limited and may be the means described in the preferred mode of causing a microparticle to pass through the through-hole of the substrate according to the present invention. For example, an electrophoresis means, an optical tweezers means, and the like may be used. The electrophoresis means can include a first liquid tank that is filled with an electrolytic solution together with a surface having at least a through-hole on one surface side of the above-described substrate, a second liquid tank that is filled with an electrolytic solution together with a surface having at least the through-hole on the other surface side of a substrate, a first electrode formed in the first liquid tank (and can be disposed in a liquid filled), a second electrode formed in the second liquid tank (and can be disposed in a liquid filled), and a power supply for applying voltage to the first electrode and the second electrode.

(Analysis Means and Others)

The apparatus for measuring a spectrum of a microparticle may include: analysis means for implementing the above-described analysis method for a microparticle (such as a program that makes a principal component analysis and performs correlation coefficient mapping); control means, such as a general-purpose CPU or a processor, for executing the analysis means; storage means storing the analysis means; recording means, such as a memory and a RAM, that records the obtained measured spectrum and other data; input means, such as a mouse and a keyboard; output means; display means, such as a display; and other software or hardware. One or some of these may be stored in a PC or may be stored on a cloud system.

Embodiment

Hereinafter, the present invention will be further specifically described with reference to the embodiment. Materials, reagents, amounts of substances and their ratios, operations, and the like described in the following embodiment may be changed as needed without departing from the purport of the present invention. Therefore, the scope of the present invention is not limited to the following embodiment.

<Preparation of Substrate>

Figure 1B:
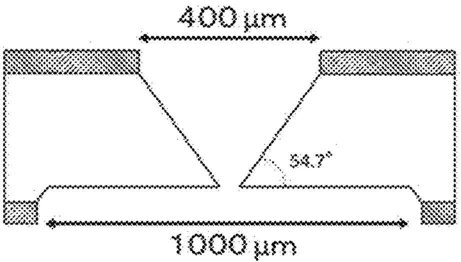
Figure 1C:
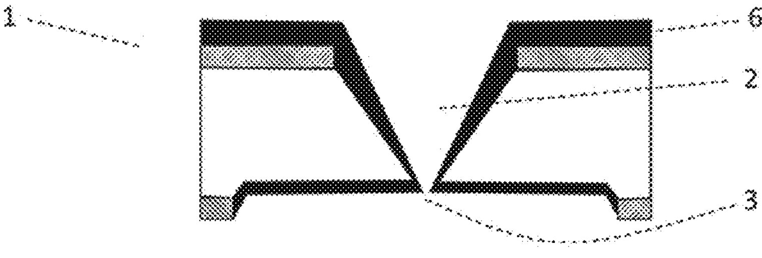

A silicon wafer (E&M CO., LTD) (FIG. 1A) with a plane direction of (100) and a thickness of 300 μm, having 50 nm silicon nitride (silicon nitride) film on both surfaces was cut into 25 mm square. A metal mask for preventing etching with a 400 μm by 400 μm square-shaped through-hole was put over one surface of a substrate, the silicon nitride film was removed only in the 400 μm by 400 μm square-shaped region exposed to the inside of the through-hole by a reactive ion etching apparatus (RIE-10NR, SAMCO CO., Ltd), and a silicon surface was made bare only in the 400 μm by 400 μm square-shaped region. The silicon nitride film was removed only in a 1000 μm by 1000 μm square-shaped region similarly on the other surface of the substrate at an opposed location as well, and a silicon surface was made bare only in the 1000 μm by 1000 μm square-shaped region. After that, only silicon at the bare part of the 400 μm by 400 μm silicon surface (surface A) was selectively subjected to wet etching on a 125° C. hot plate (Hot plate NINOS ND-1, As One CO., Ltd) for about three hours by using potassium hydroxide aqueous solution (Wako Pure Chemical Industries, Ltd.). After that, only silicon at the bare part of the other-side 1000 μm square silicon surface (surface B) of the substrate was selectively subjected to wet etching on the 125° C. hot plate until the through-hole was perforated in the silicon substrate by using potassium hydroxide aqueous solution (Wako Pure Chemical Industries, Ltd.). With this operation, a silicon through-hole having a shape (tapered structure) such that a width of the through-hole continuously reduces from one surface of the substrate to the other surface of the substrate was formed (FIG. 1B). After that, 100 nm Au that is a metal that exhibits plasmon resonance was vapor deposited from the top and bottom surface sides of the substrate by sputtering (SVC-700LRF, Sanyu Electron Co., Ltd.) (FIG. 1C).

Figure 2:
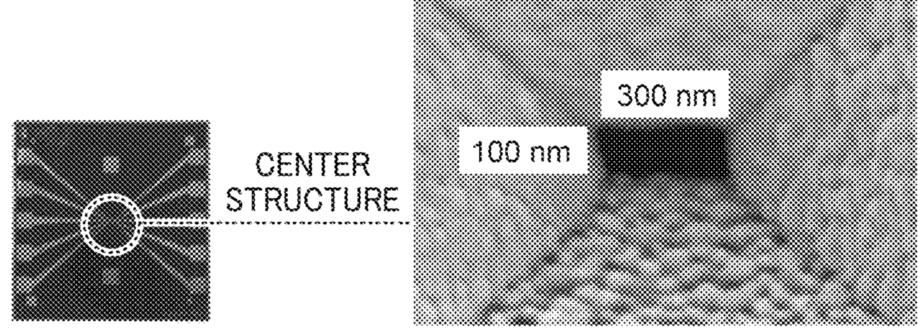
FIG. 2 is a view showing the structure of the substrate used in the embodiment.

FIG. 2 is a photograph showing surface A side of the prepared substrate and a scanning electron micrograph of the through-hole part of the substrate. The opening portion of the through-hole was a 100 nm by 300 nm rectangle. The angle that the tapered surface of the through-hole (the lateral face of the quadrangular pyramid frustum) makes with the surface of the substrate was 54.7 degrees (FIG. 1B).

Figure 3:
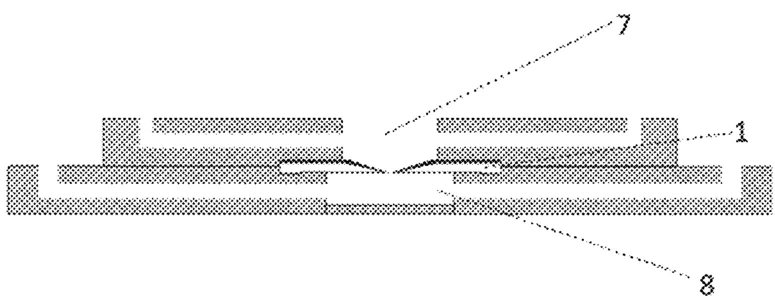
FIG. 3 is a schematic sectional view of a device for measuring a spectrum, used in the embodiment.

With the configuration shown in FIG. 3, liquid tanks (a first liquid tank and a second liquid tank) were respectively formed on one surface (surface A) side and the other surface (surface B) side of the prepared substrate to provide a device for measuring a microparticle. Each of the liquid tanks was made of a hydrophilic resin such that a part of the substrate surface, including the through-hole, was part of the inner wall.

<Preparation of Exosome Sample>

An exosome that was a biogenic microparticle having a lipid bilayer membrane was used as a microparticle sample.

(1) A culture supernatant fluid of normal cells (TIG-3 (human lung-derived adherent cells); American Type Culture Collection Co., Ltd., America) was collected and subjected to centrifugation with a centrifuge for 15 minutes under the condition of 4° C. at 3000Gs to remove dead cells and cell fragments. This was used as a culture supernatant sample.

(2) 20 mL of the culture supernatant sample was introduced into an ultracentrifuge-specific centrifugal tube and subjected to centrifugal treatment for 80 minutes under the condition of 4° C. at 110000Gs.

(3) Attention was paid so that a pipet did not touch the inner wall of the tube that is located on the outer side in centrifugal treatment, a supernatant was removed, and a deposit on the inner wall of the tube that is located on the outer side in centrifugal treatment was dispersed through multiple times of pipetting by using 1 mL of PBS (made by Nippon Gene Co., Ltd.) filtrated with a 0.22 μm filter.

(4) 19 mL of PBS was added, and centrifugal treatment was performed again for 80 minutes under the condition of 4° C. at 110000Gs.

(5) Attention was paid so that a pipet did not touch the inner wall of the tube that is located on the outer side in centrifugal treatment, a supernatant was removed, and a deposit was dispersed enough with 1 mL of PBS to provide a normal cell-derived exosome sample.

(6) Except that liver cancer cell-derived cells (HepG2 (human liver cancer cells); American Type Culture Collection Co., Ltd., America) were used instead of normal cells, a liver cancer-derived exosome sample was prepared in accordance with a procedure similar to preparation of the normal cell-derived exosome sample.

<Measurement of Raman Spectra of Exosomes>

Figure 4:
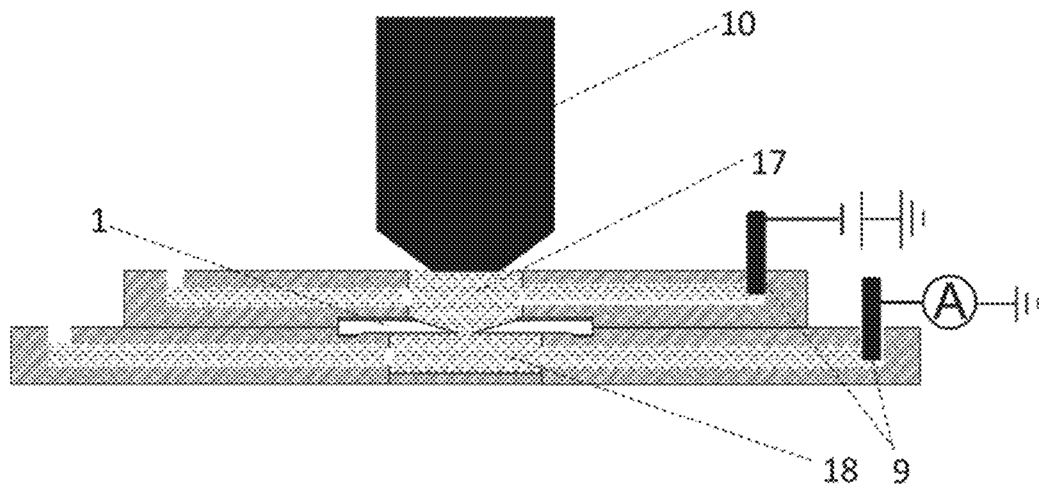
FIG. 4 is a schematic sectional view of a Raman spectrum measurement system used in the embodiment.
Figure 5:
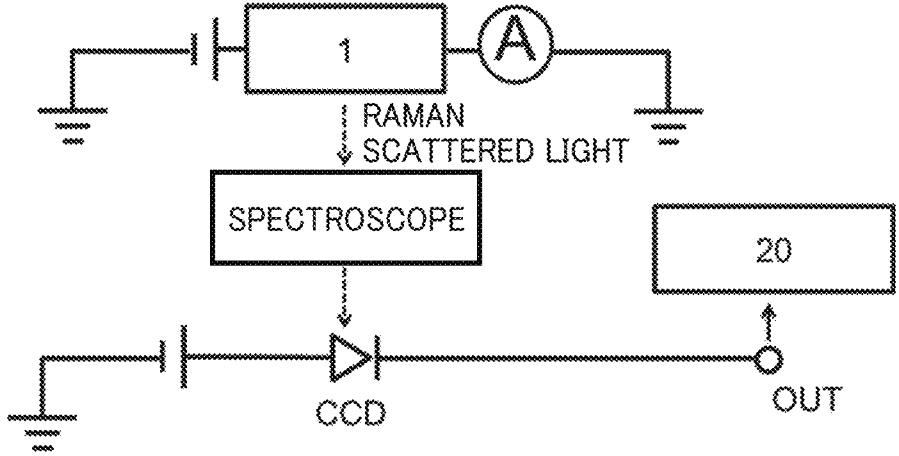
FIG. 5 is a circuit block diagram of the Raman spectrum measurement system used in the embodiment.

The first liquid tank and the second liquid tank of the prepared device were filled with TE buffer (Tris-EDTA buffer: made by Nippon Gene Co., Ltd.) serving as an electrolytic solution. Furthermore, a silver-silver chloride electrode was disposed in each of the liquid tanks. The prepared exosome sample was added to the electrolytic solution in the first liquid tank. The device was set on the stage of a HORIBA Raman spectroscopy apparatus (name: LabRAM ARAMIS), and a measurement system shown in FIGS. 4 and 5 was constructed. An immersion-type objective lens was disposed on the first liquid tank such that the distance from the through-hole to the surface of the objective lens was 2 mm. Measurement was performed with 785 nm laser.

By applying a voltage of 0.1 V to the electrodes disposed in the liquid tanks, exosomes in the first liquid tank were guided into the through-hole by using electrophoresis and caused to pass through the through-hole of the substrate one by one. Furthermore, while the passage speed of a microparticle was being adjusted with optical tweezers (using 785 nm laser for Raman measurement), the microparticle was held inside the through-hole so that the microparticle was decelerated inside the through-hole while being adsorbed inside the through-hole, and caused to pass through the through-hole. Laser was applied from the surface side having a larger opening portion of the through-hole for one to 10 seconds per microparticle, a spectrum of 400 cm$^{-1}$ to 1600 cm$^{-1}$ was measured with a resolution of 1 cm$^{-1}$ to obtain a Raman spectrum at the location of the through-hole. After measurement, light was turned off to peel off the particle. After the held microparticle was removed from inside the through-hole, the next microparticle was measured. A plurality of measured Raman spectra each one by one for a microparticle was obtained by repeating this procedure.

Figure 6:
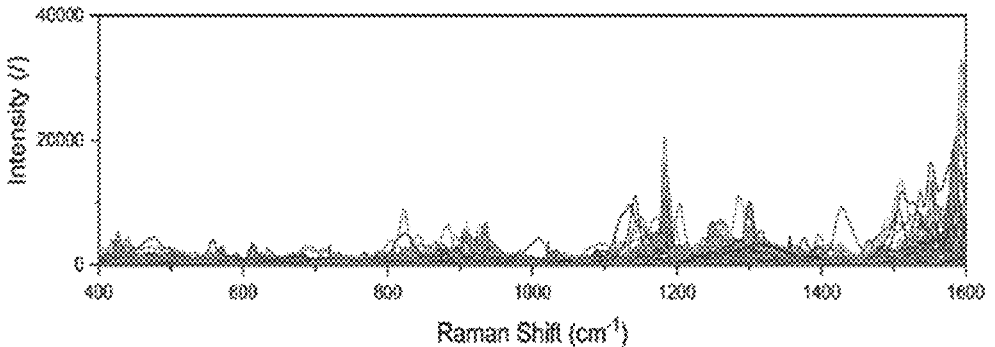
FIG. 6 is a graph overlappingly showing measured Raman spectra of a plurality of (N=100) microparticles in a normal cell-derived exosome sample.
Figure 7:
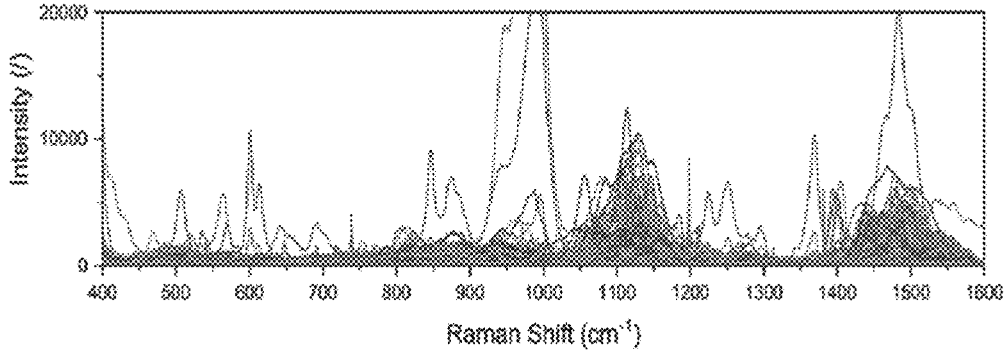
FIG. 7 is a graph overlappingly showing measured Raman spectra of a plurality of (N=155) microparticles in a liver cancer cell-derived exosome sample.

One hundred microparticles were measured for the normal cell-derived exosome sample, 155 microparticles were measured for the liver cancer cell-derived exosome sample, and spectral data that is a bundle of 100 measured spectra and spectral data that is a bundle of 155 measured spectra were respectively obtained from the samples. In other words, according to the present invention, it is found that spectral data for an analysis using microparticles with a length less than or equal to 5 μm can be generated from microparticles one by one. FIG. 6 is a result overlappingly showing a plurality of Raman spectra measured for the normal cell-derived exosome sample. FIG. 7 is a result overlappingly showing a plurality of Raman spectra measured for the liver cancer cell-derived exosome sample. It appears that, from the result of the liver cancer cell-derived exosome sample, a signal is observed around 1100 cm$^{-1}$ in the spectra of a large number of microparticles.

<Data Analysis with Correlation Coefficient>

The intensity of Raman scattered light observed was normalized (a maximum in each spectrum was set to one) for the spectral data obtained as described above of each sample, and then an N-by-M matrix was formed. N denotes the number of spectra (100 or 155), and M denotes Raman spectrum points (1200 each) obtained by dividing 400 cm$^{-1}$ to 1600 cm$^{-1}$ by the measurement resolution 1 cm$^{-1}$. In a Raman spectrum group (N) of each sample, a correlation coefficient of the intensity between two Raman shift points (Y and Y') was obtained by using the following expression.

CORRELATION FUNCTION $R_{YY'}$ [1]

$$R_{YY'} = \frac{S_{YY'}}{S_Y \cdot S_{Y'}}$$

$$Y = 1, 2, 3, \ldots M$$

$$Y' = 1, 2, 3, \ldots M$$

$$S_{YY'} = \frac{1}{N}\sum_{i=1}^{N}(X_{i \cdot Y} - m_Y)(X_{i \cdot Y'} - m_{Y'})$$

$m_Y$: MEAN OF $Y$ LINE $m_{Y'}$: MEAN OF $Y'$ LINE $$S_Y = \sqrt{\frac{1}{N}\sum_{i=1}^{N}(X_{i \cdot Y} - m_Y)^2}$$

$$S_{Y'} = \sqrt{\frac{1}{N}\sum_{i=1}^{N}(X_{i \cdot Y'} - m_{Y'})^2}$$

Figure 8:
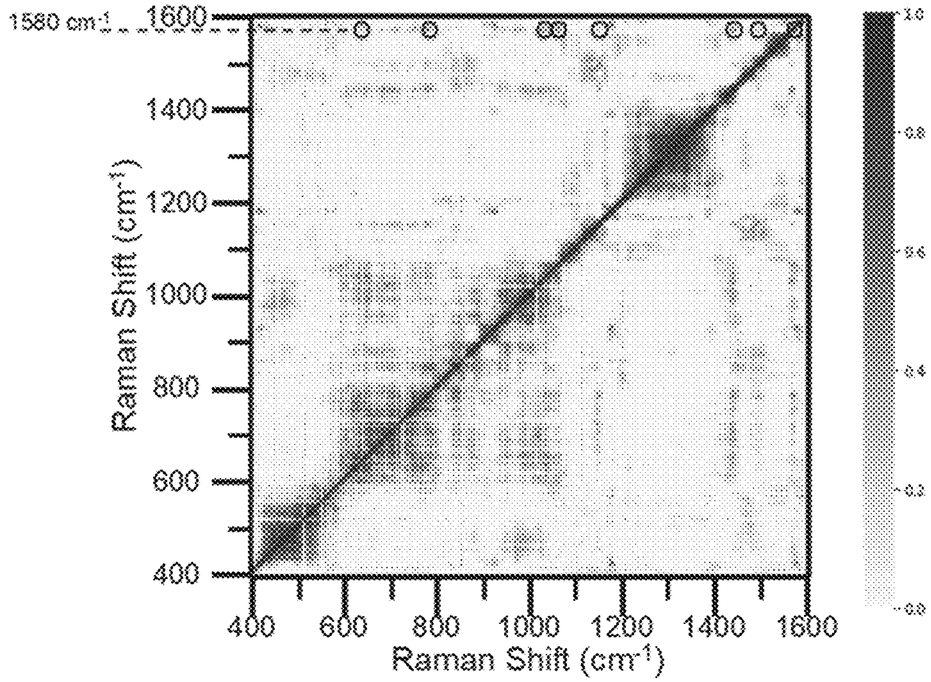
FIG. 8 is a graph showing a result obtained by mapping correlation coefficients of measured Raman spectra of a plurality of microparticles in a normal cell-derived exosome sample.

A correlation coefficient was obtained for all the combinations of YY', and mapping of the correlation coefficients was performed. The result is shown in FIG. 8. FIG. 8 is the result of the normal cell-derived exosome sample. In mapping of correlation coefficients shown in the graph, the intensity of color increases as the correlation coefficient increases. In the result of the normal cell-derived exosome sample of FIG. 8, peaks at 1580 cm$^{-1}$ that indicate a high correlation coefficient (higher than or equal to 0.5) are surrounded by circles. These peaks are moving in synchronization with one another, so these are considered to be signals from the same molecules. The peak group coincides with the peaks of integrin molecule (α5B1) (NPL 5), so the peak group is presumably derived from integrin molecule.

[NPL 5] Mustafa H. Chowdhury, et al., "Use of surface-enhanced Raman spectroscopy for the detection of human integrins", Journal of Biomedical Optics, Vol. 11, 024004.

Figure 9:
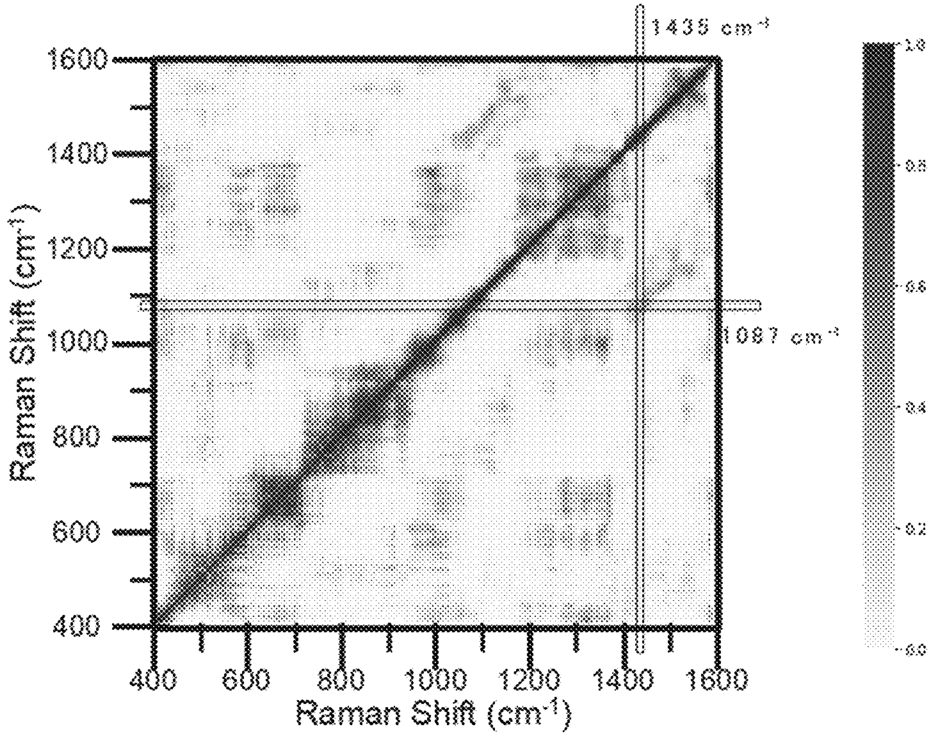
FIG. 9 is a graph showing a result obtained by mapping correlation coefficients of measured Raman spectra of a plurality of microparticles in a liver cancer cell-derived exosome sample.

Furthermore, FIG. 9 is the result of mapping of correlation coefficients of the liver cancer cell-derived exosome sample (data of FIG. 7 (155 spectra)). The intensity of color at the position where around 1087 $cm^{-1}$ and around 1435 $cm^{-1}$ intersect with each other is high, so it is found that these peaks synchronize with each other. A signal around 1087 cm 1 is a peak that can also be obtained from non-phosphorylated protein; however, the signal synchronizes with around 1435 $cm^{-1}$, so it turns out that this was a signal derived from phosphorylated protein (phosphoserine).

<Principal Component Analysis>

Figure 10:
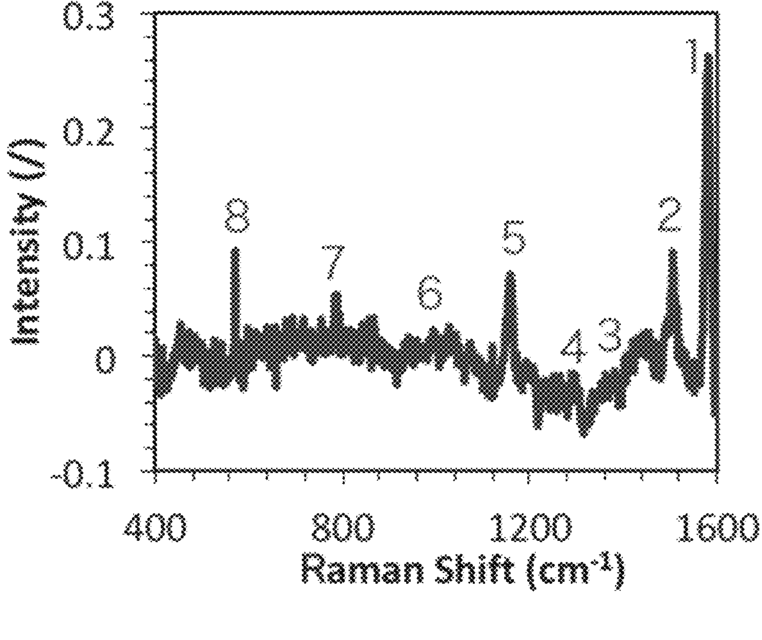
FIG. 10 is a graph showing the spectrum of a first principal component, obtained by making a principal component analysis of measured Raman spectra of a plurality of microparticles in a normal cell-derived exosome sample.

A principal component analysis was made by using the N-by-M matrix generated similarly to the above. FIG. 10 (normal cell-derived exosome sample) shows the obtained spectrum (eigenvector) of the first principal component. The peaks in the obtained spectrum all coincided with data of integrin (α5ß1).

Figure 11:
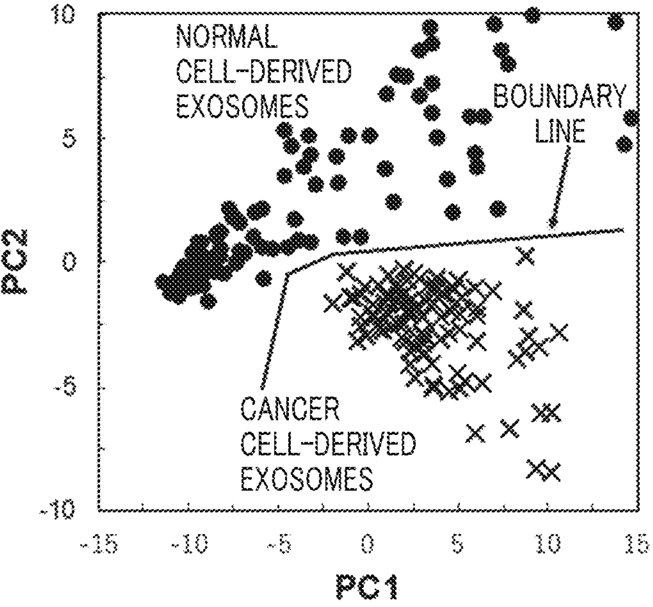
FIG. 11 is a graph obtained by plotting a first principal component score and a second principal component score based on a principal component analysis of measured Raman spectra of a plurality of microparticles in a liver cancer cell-derived exosome sample and in a normal cell-derived exosome sample on the assumption that the abscissa represents the first principal component score and the ordinate represents the second principal component score.

Spectral data that is a bundle of 255 ($N_1+N_2$) measured spectra was prepared by using the spectral data ($N_1$: 100 spectra) obtained from the normal cell-derived exosome sample and the spectral data ($N_2$: 155 spectra) obtained from the liver cancer cell-derived exosome sample, obtained as described above. Where data points of spectrum were 1200 (M), a principal component analysis was made by using the 255-by-1200 matrix based on the spectral data, and eigenvectors of the first principal component to the 100th principal component were obtained by using a program created in accordance with python. FIG. 11 shows the result of score plots of the first principal component (PC1) and the second principal component (PC2). As indicated by the boundary line in the graph, it turns out that the measured spectra of the normal cell-derived exosomes and the measured spectra of the liver cancer cell-derived exosomes can be recognized from the result of the plots.

<Principal Component Analysis of Raman Spectra of X-Ray Irradiated Cell-Derived Exosomes>

Figure 12:
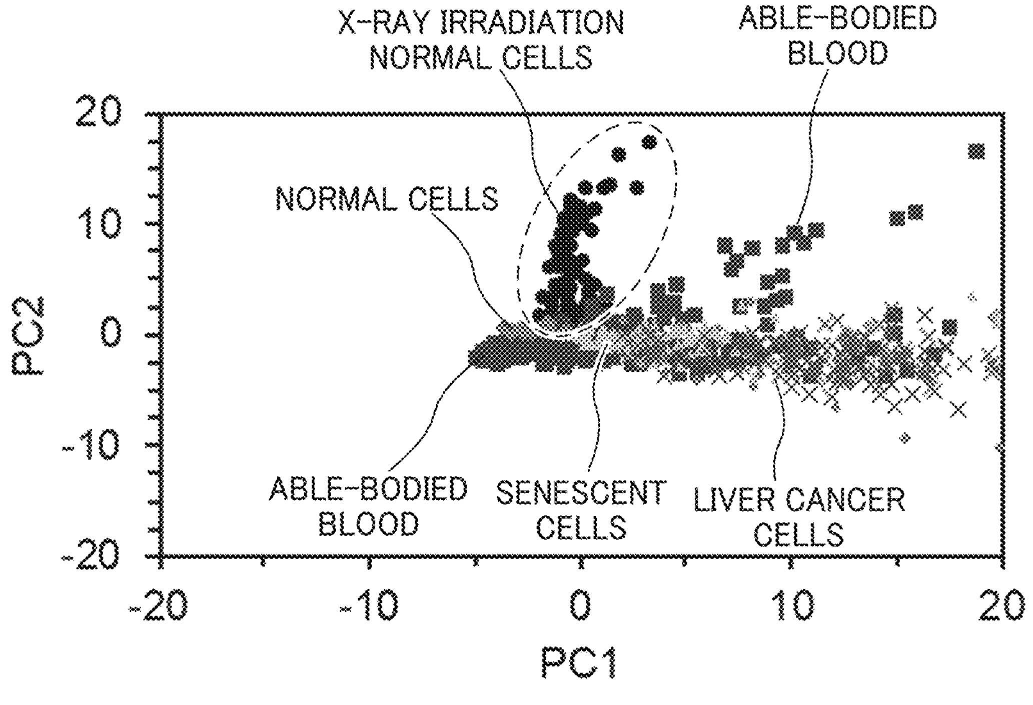
FIG. 12 is a graph obtained by plotting a first principal component score and a second principal component score based on a principal component analysis of measured Raman spectra of a plurality of microparticles in an exosome sample derived from a normal cell, an X-ray irradiated normal cell, a liver cancer cell, blood of the able-bodied, and a senescent cell on the assumption that the abscissa represents the first principal component score and the ordinate represents the second principal component score.

With a procedure similar to the above, Raman spectra of normal cell (TIG-3)-derived exosomes, X-ray irradiated normal cell (TIG-3)-derived exosomes, liver cancer cell (HepG2)-derived exosomes, exosomes derived from blood of the able-bodied, and senescent cell-derived exosomes were measured and subjected to a principal component analysis. FIG. 12 shows the result of score plots of the first principal component (PC1) and the second principal component (PC2). In FIG. 12, the black circle mark represents an X-ray irradiated normal cell-derived exosome, the light gray rhombus mark represents a normal cell-derived exosome, the deep gray square mark represents an able-bodied blood-derived exosome, the light gray triangle mark represents a senescent cell-derived exosome, and the deep gray cross mark represents a liver cancer cell-derived exosome.

As indicated by the dashed line in FIG. 12, it turns out from the result of the plots that measured spectra of X-ray irradiated normal cell-derived exosomes and measured spectra of other exosomes can be recognized. This means that the surface molecules of X-ray irradiated normal cell-derived exosomes significantly differ from the surface molecules of other exosomes.

Fragmented pieces of DNA are contained in X-ray irradiated cell-derived exosomes, and it is known that cells transform as the DNA fragments increase in the cells. For this reason, a transformation tendency of cells is found by detecting exosomes in which fragmented pieces of DNA are contained (X-ray irradiated normal cells in FIG. 12). This can diagnose a change in the body before getting cancer, so it is useful for preventive healthcare.

<Measurement of Raman Spectra of Silica Microparticles>

Figure 13:
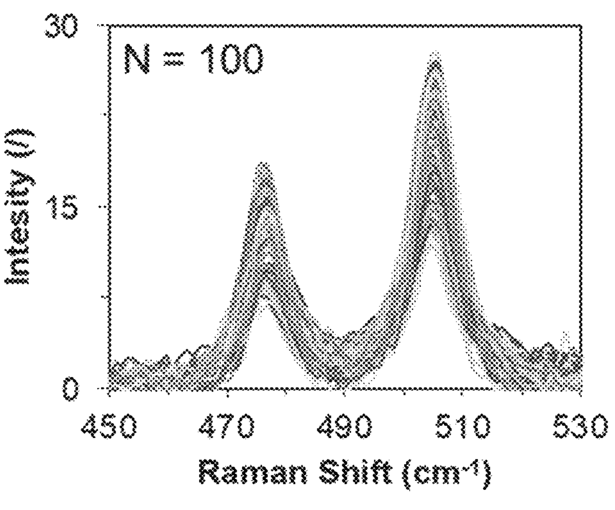
FIG. 13 is a graph overlappingly showing measured Raman spectra of a plurality of (N=100) silica microparticles.

Silica microparticles that are inorganic microparticles of PM2.5 were used as a microparticle sample. Raman spectra of silica microparticles (COREFRONT Corporation) with a diameter of 100 nm were measured in accordance with a similar procedure by using the same substrate as that at the time of measurement of the exosome samples, and spectral data that is a bundle of 100 measured spectra was obtained. In other words, according to the present invention, it is found that spectral data for an analysis using microparticles with a length less than or equal to 5 μm can be generated from microparticles one by one. FIG. 13 shows a result overlappingly showing measured Raman spectra of a plurality of (N=100) silica microparticles. It appears from FIG. 13 that, in the result of a highly uniform silica microparticle sample, a signal having a local maximum around 478 $cm^{-1\pm5}$ $cm^{-1}$ and a local maximum around 506 $cm^{-1\pm5}$ $cm^{-1}$ is observed in all the spectra of the microparticles. These peaks are derived from silica (NPL 6), so it appears that the microparticles are measured properly and highly reproducible data is obtained.

[NPL 6] Kazunori Matsui, et al., "Raman Spectra of Silica Gel Prepared from Triethoxysilane and Tetraethoxysilane by the Sol-Gel Method", Journal of the Ceramic Society of Japan, Vol. 106, pp. 528-530.

By using the spectral data of silica microparticles, acquired with the generation method according to the present invention, as a new database obtained in the present invention or by performing the above-described principal component analysis or the like in combination with spectral data of other PM2.5 particles, acquired by similarly applying the generation method according to the present invention to other PM2.5 particles, it is possible to discriminate the type of PM2.5 in the atmosphere and apply the technique to an analysis of air pollution situation.

<Measurement of Fluorescent Spectra of Gold Microparticles>

Figure 14:
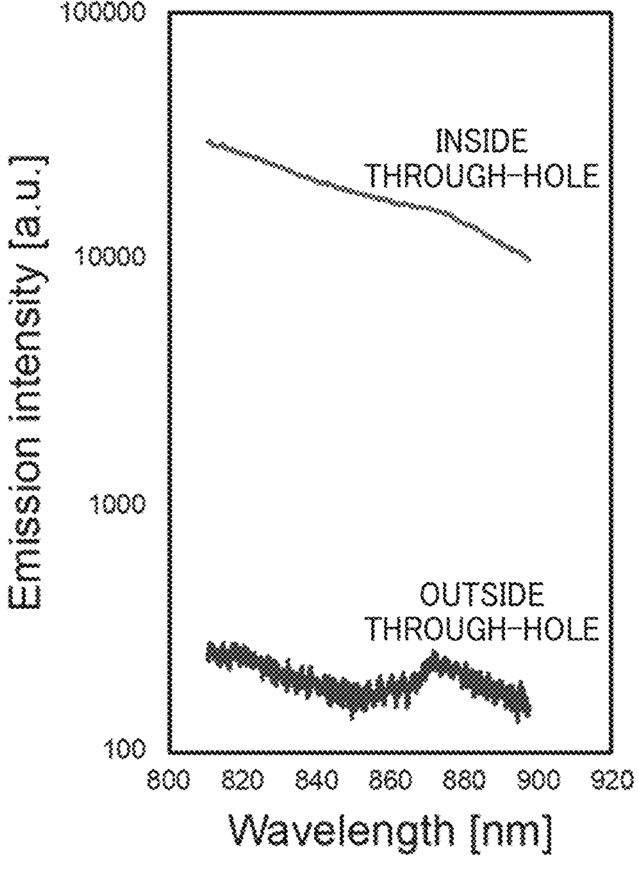
FIG. 14 is a graph overlappingly showing measured fluorescent spectra of gold microparticles inside and outside a through-hole.

Gold microparticles with a diameter of 20 nm to 100 nm, in which the surfaces of inorganic microparticles were coated with gold, were used as a microparticle sample. A fluorescent spectrum of each gold microparticle trapped in the through-hole in a similar procedure was measured (excitation wavelength 532 nm) with the same substrate as that at the time of measurement of the exosome samples. FIG. 14 shows a measured fluorescent spectrum of one gold microparticle outside the through-hole and a measured fluorescent spectrum of one gold microparticle in the through-hole. It appears from FIG. 14 that, when a fluorescent spectrum is measured in the through-hole of the substrate according to the present invention, fluorescence from the gold microparticle can be increased. Since the peak wavelength of fluorescence of the gold microparticle is shorter than or equal to 800 nm, the graph shows a part at the long wavelength-side bottom of the fluorescent spectrum.

The subject application claims the benefit of priority based on Japanese Patent Application No. 2021-188402 filed on Nov. 19, 2021. The disclosure of the specification and drawings of the Japanese Patent Application is incorporated in the specification of the present application in its entirety.

INDUSTRIAL APPLICABILITY

The present invention is useful in various fields, such as determination of a type of microparticle, determination of a possibility of disease, and analysis of air pollution situation.

REFERENCE SIGNS LIST

1 Substrate
2 Through-hole
3 Opening portion
4 Silicon
5 Silicon nitride film
6 Gold (Au) layer
7 First liquid tank
8 Second liquid tank
9 Electrode
10 Immersion objective lens
17 First liquid tank filled with electrolytic solution
18 Second liquid tank filled with electrolytic solution
20 Analysis means

The invention claimed is:

1. A generation method for spectral data of a microparticle sample containing a plurality of microparticles, the generation method comprising:

acquiring a measured spectrum from each of the plurality of microparticles by causing the plurality of microparticles to pass through a through-hole of a substrate one by one while applying light into the through-hole, wherein the through-hole has a tapered structure in which a width continuously reduces from one surface of the substrate to another surface of the substrate, the through-hole has a shape of a quadrangular pyramid frustum, at least part of an inner surface of the through-hole is made of a metal that exhibits plasmon resonance, in acquiring the measured spectrum, the measured spectrum is acquired each time a single microparticle passes through the through-hole, and the spectral data are a bundle of a plurality of the measured spectra.

2. The generation method according to claim 1, wherein a length of the microparticle ranges from 10 nm to 5 μm.

3. The generation method according to claim 1, wherein the acquiring a measured spectrum includes moving the microparticle, dispersed in a liquid, into the through-hole with one or more methods selected from the group consisting of electrophoresis, dielectrophoresis, optical tweezers, Brownian movement, and Coulomb interaction.

4. The generation method according to claim 1, wherein the measured spectrum is a Raman spectrum.

5. The generation method according to claim 1, wherein the measured spectrum is a fluorescent spectrum.

6. An analysis method for a microparticle, comprising making a statistical analysis of the spectral data acquired with the generation method according to claim 1.

7. The analysis method according to claim 6, wherein the making a statistical analysis of the spectral data includes forming a collection of peaks having a high correlation coefficient with each other between the plurality of measured spectra of the spectral data, and identifying at least one component contained in the microparticles by comparing the obtained collection of peaks with a spectrum of a known object.

8. The analysis method according to claim 6, wherein the making a statistical analysis of the spectral data includes making a multivariate analysis on the plurality of measured spectra of the spectral data, and identifying at least one component contained in the microparticles by comparing a spectrum, obtained through the multivariate analysis, with a spectrum of a known object.

9. A discrimination method of discriminating a yet-to-be discriminated microparticle, the discrimination method comprising:

acquiring a measured spectrum of each of a plurality of microparticles A of which a type has been turned out and a measured spectrum of each of a plurality of microparticles B of which another type has been turned out, with the generation method according to claim 1;

making a principal component analysis of spectral data including the measured spectra of the plurality of microparticles A and the measured spectra of the plurality of microparticles B and obtaining an index to discriminate the measured spectrum of the microparticle A and the measured spectrum of the microparticle B from scores of two or more principal components;

acquiring a measured spectrum from each of one or more yet-to-be discriminated microparticles in a microparticle sample with the generation method according to claim 1;

calculating scores of the two or more principal components for the measured spectrum of the yet-to-be discriminated microparticle; and performing discrimination by comparing the scores of the yet-to-be discriminated microparticle with the index, wherein a length of the yet-to-be discriminated microparticle ranges from 10 nm to 5 μm.

10. The discrimination method according to claim 9, wherein the yet-to-be discriminated microparticle is an exosome, the microparticles A are cancer cell-derived exosomes, the microparticles B are normal cell-derived exosomes, and the performing discrimination includes discriminating whether the exosome serving as the yet-to-be discriminated microparticle is derived from a cancer cell.

11. A determination method of determining presence or absence of a cancer cell-derived exosome in a body fluid-derived sample containing exosomes, the determination method comprising:

generating spectral data made up of a plurality of measured spectra respectively obtained from a plurality of exosomes in the sample with the generation method according to claim 1;

obtaining a correlation coefficient between a signal having a local maximum at $1087\ cm^{-1} \pm 5\ cm^{-1}$ and a signal having a local maximum at $1435\ cm^{-1} \pm 5\ cm^{-1}$ between the plurality of measured spectra; and determining that a cancer cell-derived exosome is present in the sample when the correlation coefficient is higher than or equal to a certain value.

12. An apparatus for acquiring spectral data of a microparticle sample containing a plurality of microparticles, the apparatus comprising:

a device that includes a substrate having a through-hole;

a guiding section for causing the microparticle to pass through the through-hole one by one;

a light source; and a detecting section that acquires a measured spectrum by measuring light that is generated when light from the light source is applied to the microparticle in the through-hole, wherein the through-hole has a tapered structure in which a width continuously reduces from one surface of the substrate to another surface of the substrate, the through-hole has a shape of a quadrangular pyramid frustum, at least part of an inner surface of the through-hole is made of a metal that exhibits plasmon resonance, when the light source applies the light into the through-hole of the substrate, the guiding section causes the plurality of microparticles to pass through the through-hole one by one, and the detecting section acquires a measured spectrum from each of the plurality of microparticles, and the spectral data are a bundle of a plurality of the measured spectra.

13. The apparatus according to claim 12, wherein the measured spectrum is a Raman spectrum.

14. The apparatus according to claim 12, wherein the measured spectrum is a fluorescent spectrum.

15. The generation method according to claim 1, wherein an upper-side opening portion and a lower-side opening potion of the through-hole have a quadrangular shape.

16. The apparatus according to claim 12, wherein an upper-side opening portion and a lower-side opening potion of the through-hole have a quadrangular shape.

* * * * *